Figure 1:
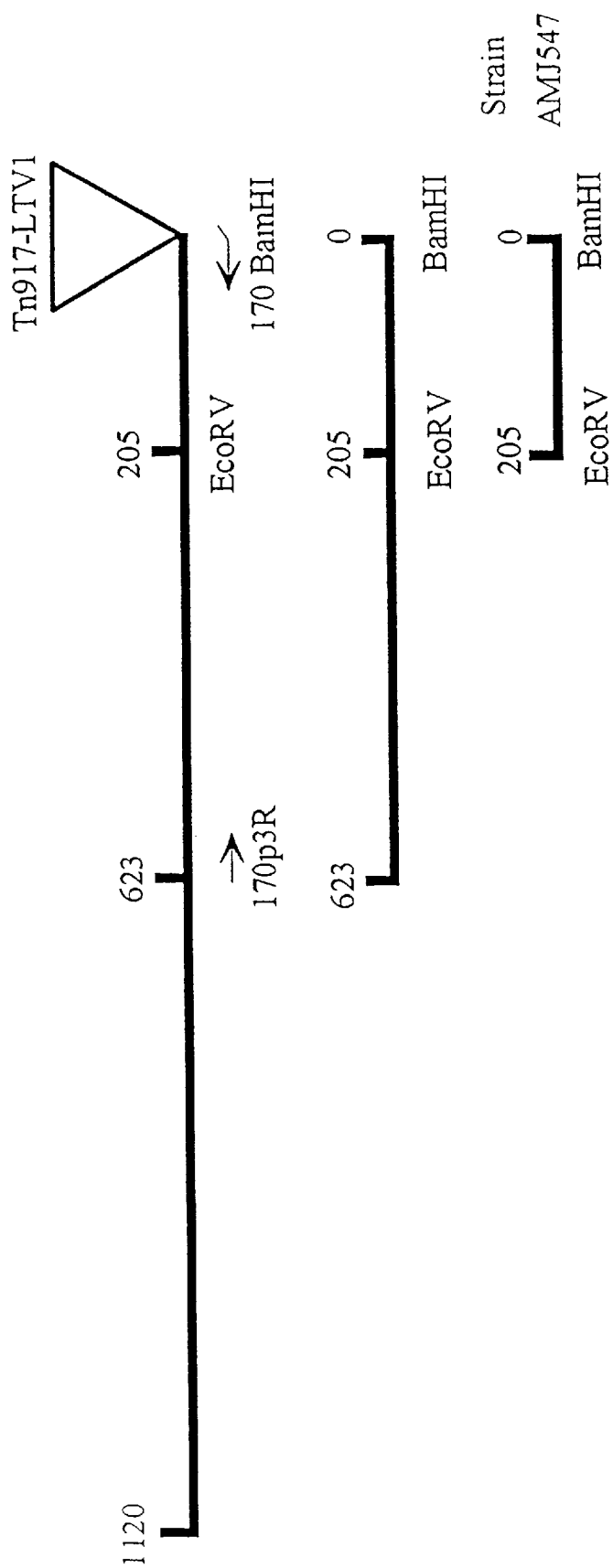

US006133023A

United States Patent [19]
Madsen et al.

[11] Patent Number: 6,133,023
[45] Date of Patent: Oct. 17, 2000

[54] LACTIC ACID BACTERIAL REGULATABLE EXPRESSION SYSTEM

[75] Inventors: Soeren Michael Madsen, Copenhagen; Astrid Vrang, Lyngby; José Arnau, Hellerup; Peter Ravn, Naerum; Mads Groenvald Johnsen, Frederiksberg; Hans Israelsen, Alleroed, all of Denmark

[73] Assignee: Bioteknologisk Institut, Hoersholm, Denmark

[21] Appl. No.: 08/981,601

[22] PCT Filed: Aug. 22, 1997

[86] PCT No.: PCT/DK97/00341

§ 371 Date: Dec. 29, 1997

§ 102(e) Date: Dec. 29, 1997

[87] PCT Pub. No.: WO98/10079

PCT Pub. Date: Mar. 12, 1998

Related U.S. Application Data

[63] Continuation-in-part of application No. 08/711,434, Sep. 6, 1996, abandoned.

[51] Int. Cl.$^7$ .............................. C12N 15/00; C12N 7/00; C12N 1/20; C12P 19/34
[52] U.S. Cl. ................................... 435/320.1; 435/252.3; 435/69.1; 435/91.1; 435/235.1
[58] Field of Search ............................... 435/69.1, 252.3, 435/320.1, 91.1, 235.1

[56] References Cited

U.S. PATENT DOCUMENTS

| 5,837,509 | 11/1998 | Israelsen et al. | 435/91.1 |
| 5,853,718 | 12/1998 | Molin et al. | 424/93.2 |

FOREIGN PATENT DOCUMENTS

| 0 449 770 A2 | 2/1991 | European Pat. Off. . |
| 0 449 770 | 10/1991 | European Pat. Off. . |
| 0 712 935 A2 | 11/1995 | European Pat. Off. . |
| 92-04451 | 3/1992 | WIPO . |
| 94/16086 | 7/1994 | WIPO . |
| WO 94/16086 | 7/1994 | WIPO . |
| 95-31563 | 11/1995 | WIPO . |

OTHER PUBLICATIONS

Smith, Elements of Molec.Neurobiology, 2nd ed., p. 74–82, 1996.
Darnell et al, Molec.Cell Biology, p. 400–401, 1986.
Israelsen et al, Appl.Envir.Microbiology 61:2540–2547, Jul. 1995.
Andersen et al., "MPB64 Possesses Tuberculosis–Complex–Specific B– and T–Cell Epitopes", Scand. J. Immunol., vol. 34, pp. 365–372, (1991).
Jensen et al., "Minimal Requirements for Exponential Growth of *Lactococcus Lactis*", Applied and Environmental Microbiology, vol. 59, No. 12, pp. 4363–4366, (19930.
Klausen et al., Characterization of Purified Protein Derivative of Tuberculin by Use of Monoclonal Antibodies: Scand. J. Immunol., vol. 40, pp. 345–349, (1994).

Oettinger et al., "Cloning and B–Cell–Epitope Mapping of MPT64 From *Mycobacterium Tuberculosis* H37Rv", Infection and Immunity, vol. 62, No. 5, pp. 2058–2064, (1994).
Oettinger et al., "Mapping of the Delayed–Type Hypersensitivity–Inducing Epitope of Secreted Protein MPT64 from *Mycobacterium Tuberculosis*", Infection and Immunity, vol. 63, No. 12, pp. 4613–4618.
Sorensen et al., Purification and Characterization of a Low–Molecular–Mass T–Cell Antigen Secreted by Infection and Immunity, vol. 63, No. 5, pp. 1710–1717.
Ballester, Selective Advantage of Deletions Enhancing Chloramphenicol Acetyltransferase Gene Expression in Elsevier Science Publishers, Gene, vol. 41, No. 2/3, pp. 153–163.
Z. Alexieva et al., "Chloramphenicol Induction of cat–86 Requires Ribosome Stalling at a Specific Site in the Leader", Proc. Natl. Acad. Sci. USA, vol. 85, May 1988, pp. 3057–3061.
E. Bidnenko et al., "Phage Operon Involved in Sensitivity to the *Lactococcus lactis* Abortive Infection Mechanism AbiD1", Journal of Bacteriology, Jul. 1995, pp. 3824–3829.
C. Chiaruttini et al., "Gene Organization, Primary Structure and RNA Processing Analysis of a Ribosomal RNA Operon in *Lactococcus lactis*", J. Mol. Biol., vol. 230, 1993, pp. 57–76.
S. David et al., "*Leuconostoc lactis* β–Galactosidase is Encoded by Two Overlapping Genes", Journal of Bacteriology, vol. 74, No. 13, Jul. 1992, p. 4475–4481.
P. de Ruyter et al., " Functional Analysis of Promoters in the Nisin Gene Cluster of *Lactococcus lactis*", Journal of Bacteriology, vol. 178, No. 12, Journal of Bacteriology, Jun. 1996, pp. 3434–3439.
M. Gasson, "Plasmid Complements of *Streptococcus lactis* NCDO 712 and Other Lactic Streptococci After Protoplast–Induced Curing", Journal of Bacteriology, vol. 154, No. 1, Apr. 1983, p. 1–9.

(List continued on next page.)

*Primary Examiner*—Ali Salimi
*Attorney, Agent, or Firm*—Foley & Lardner

[57] ABSTRACT

Expression vectors capable of being replicated in lactic acid bacterial cells comprising a promoter region comprising (a) a promoter sequence element the function of which is regulatable by an environmental or growth condition factor and (b) at least one further nucleotide sequence element, the position, orientation, presence and/or sequence of which element has a regulatory effect on the expression of a gene operably linked to the promoter region in which vectors the position, orientation, presence and/or sequence of at least one of said elements (a) or (b) is modified relative to the position, orientation, presence and/or sequence of the corresponding non-modified element whereby the expression of the gene is altered, and a lactic acid bacterium which is transformed with such a vector as defined above are provided. The recombinant cells containing such a regulatable or inducible gene expression system are useful as food or feed starter cultures or as strains for the production of gene products such as pharmaceutically or immunologically active compounds including oligo- or polypeptides derived from a Mycobacterium species including *M. tuberculosis*.

45 Claims, 13 Drawing Sheets

OTHER PUBLICATIONS

D. Hanahan, "Studies on Transformation of *Escherichia coli* with Plasmids", J. Mol. Biol. Vol. 166 1983, pp. 557–580.

H. Holo et al., "High–Frequency Transformation ,by Electroporation, of *Lactococcus lactis* subsp. *cremoris* Grown with Glycine in Osmotically Stabilized Media", Applied and Environmental Microbiology, vol. 55, No. 12, Applied Environmental Microbiology, vol. 55, No. 12, Dec. 1989, pp. 3119–3123.

H. Israelsen et al., "Insertion of Tranposon Tn917 Derivatives into the *Lactococcus lactis* subsp. *lactis* Chromosome", Applied and Environmental Microbiology, vol. 59, No. 1, Jan. 1993, pp. 21–26.

H. Israelsen et al., "Cloning and Partial Characterization of Regulated Promoters from *Lactococcus lactis* Tn917–lacZ Integrants with the New Prometer Probe Vector, pAK80", Applied and Environmental Microbiology, vol. 61, No. 7, Jul. 1995, pp. 2540–2547.

E. Johansen et al., "Characterization of Leuconostoc Isolates from Commercial Mixed Strain Mesophilic Starter Cultures", J. Dairy Sci., vol. 75, 1992, pp. 1186–1191.

R. Kiewiet et al., "The Mode of Replication is a Major Factor in Segregational Plasmid Instability in *Lactococcus lactis*", Applied and Environmental Microbiology, vol. 59, No. 2, Feb. 1993, pp. 358–364.

Y. Le Loir et al., "Direct Screening of Recombinants in Gram–Positive Bacteria Using the Secreted Staphylococcal Nuclease as a Reporter", Journal of Bacteriology, vol. 176, No. 16, Aug. 1994, pp. 5135–5139.

F. L. Macrina et al., "Novel Shuttle Plasmid Vehicles For Escherichia–Streptococcus Transgeneric Cloning", Gene, vol. 25, 1983, pp. 145–150.

S. M. Madsen et al., "Cloning and Transcriptional Analysis of Two Threonine Biosynthetic Genes from *Lactococcus lactis* MG1614", Journal of Bacteriology, Jul. 1996, pp. 3869–3694.

J. Lawrence Marsh et al., "The pIC Plasmid and Phage Vectors with Versatile Cloning Sites for Recombinant Selection by Insertional Inactivation", Gene, vol. 32 (1984), pp. 481–485.

J. H. Miller, "Assay of β–Galactosidase", Experiments in Molecular Genetics, 1972, pp. 352–433.

A. Nauta et al., "Inducible Gene Expression Mediated by a Repressor–Operator System Isolated from *Lactococcus lactis* Bacteriophage r1t", Molecular Microbiology, vol. 19, No. 6, 1996, 1331–1341.

D. J. O'Sullivan et al., "Development of an Expression Strategy Using a Lytic Phage to Trigger Explosive Plasmid Amplification and Gene Expression", Biotechnology, vol. 14, Jan. 1996, pp. 82–87.

M. L. Pedersen et al., "Genetic Analysis of the Minimal Replicon of the *Lactococcus lactis* subsp. *lactis biovar diacetylactis* Citrate Plasmid", manuscript.

G. Simons et al., "Construction of a Promoter–Probe Vector for Lactic Acid Bacteria Using the lacG Gene of *Lactococcus lactis*", Developments in Industrial Microbiology, vol. 31, pp. 31–39.

L. Steidler et al., "Secretion of Biologically Active Murine Interleukin–2 by *Lactococcus lactis* subsp. *lactis*", Applied and Environmental Microbiology, vol. 61, No. 4, Apr. 1995, pp. 1627–1629.

M. van Asseldonk et al., Cloning of usp45, a Gene Encoding a Secreted Protein from *Lactococcus lactis* subsp. *lactis* MG1363", Gene, vol. 95, 1990, pp. 155–160.

M. van Asseldonk et al., "Cloning, Nucleotide Sequence, and Regulatory Analysis of the *Lactococcus lactis* dnaJ Gene", Journal of Bacteriology, vol. 175, No. 6, Mar. 1993, pp. 1637–1644.

M. van der Vossen et al., "Isolation and Characterization of *Streptococcus cremoris* Wg2–Specific Promoters", Applied and Environmental Microbiology, vol. 53, No. 10, Oct. 1987, pp. 2452–2457.

M. van der Vossen et al., "Construction of Cloning, Promoter–Screening, and Terminator–Screening Shuttle Vectors for *Bacillus subtilis* and *Streptococcus lactis*", Applied and Environmental Microbiology, vol. 50, No. 2, Aug. 1985, pp. 540–542.

R. J. van Rooijen et al., "Characterization of the *Lactococcus lactis* Lactose Operon Promoter: Contribution of Flanking Sequences and LacR Repressor to Promoter Activity", Journal of Bacteriology, vol. 174, No. 7, Apr. 1992, pp. 2273–2280.

J. M. Wells et al., "*Lactococcus lactis:* High–Level Expression of Tetanus Toxin Fragment C and Protection Against Lethal Challenge", Molecular Microbiology, vol. 8, No. 6, 1993, pp. 115–1162.

J. M. Wells et al., "A Model System for the Investigation of Heterologous Protein Secretion Pathways in *Lactococcus lactis*", Applied and Environmental Microbiology, vol. 59, No. 11, pp. 3954–3959.

M. W. Qoronfleh et al., "Identification and Characterization of Novel Low–Temperature–Inducible Promoters of *Escherichia coli*", Journal of Bacteriology, vol. 174, No. 24, Dec. 1992, pp. 7902–7909.

Pedersen et al., Mol. Gen. Genet. 244: 374–382 (1994).

A.

```
                                        170                        160                        150                        140
5' ATTTTTGGTTGCCATTTGCTATAAATAAAAAAACCATTTTATTGACTATATTGCAATTTATTTA
                    130                        120                        110    *              100                        90                        80                        70
CTCTCCCTAGTGCTATAAATGGCCAAAAAAAACCATTTTATTGACTATATTGCAATTTATTTA
                    60                         50                         40                         30                         20                         10                         1
CACATTATCTTTTCAGAACCAAAATCTGGCCCATTTTGGAACAGACTTCTACTATTTGTGTCTAGTA 3'
```

B.

```
         80                        70                        60
CAATTTATTTACACATTATCT              wild type sequence
         →                         →        →
         T                          T        T                 mutant no 20
         T                          T        T                 mutant no 56
                                    T                          mutant no 2 and no 59
                                    T                          mutant no 1 and no 3
```

Fig. 10

6,133,023

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:1:

```
TGAATTCAGA GGTTTGATGA CTTTGACC                                28
```

(2) INFORMATION FOR SEQ ID NO:2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:2:

```
GGAATTCCTA ACAAAAGACT ATTAACGC                                28
```

(2) INFORMATION FOR SEQ ID NO:3:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:3:

```
ATAGATCTGC AGGATCCCGG GTAACTTTGA AAGGATATTC CTC                43
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:4:

```
ATTGAGGGTA TACGGTGGGC G                                       21
```

(2) INFORMATION FOR SEQ ID NO:5:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
AAGCTTTCGC GAGCTCGAGA TCTGCAGGAT CCCGGGTAAC TTTGAAAGGA TATTCCTCAT   60
G                                                                  61
```

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Lys Leu Ser Arg Ala Arg Asp Leu Gln Asp Pro Gly
 1               5                  10
```

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Ser Phe Arg Glu Leu Glu Ile Cys Arg Ile Pro Gly Asn Phe Glu Arg
 1               5                  10                  15

Ile Phe Leu Met
             20
```

(2) INFORMATION FOR SEQ ID NO:8:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Ala Phe Ala Ser Ser Arg Ser Ala Gly Ser Arg Val Thr Leu Lys Gly
 1               5                  10                  15

Tyr Ser Ser
```

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:9:

```
GGGTCTAGAT TA                                                    12
```

(2) INFORMATION FOR SEQ ID NO:10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear -continued

```
    (ii) MOLECULE TYPE: other nucleic acid
         (A) DESCRIPTION: /desc = "Oligonucleotide"

(xi) SEQUENCE DESCRIPTION: SEQ ID NO:10:

TAATCTAGAC CC                                                            12

(2) INFORMATION FOR SEQ ID NO:11:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AAGCTTTCGC GAGCTCGAGA TCTGCAGGAT CCCGGGTCTA GATTAGGGTA ACTTTGAAAG         60

GATATTCCTC ATG                                                           73

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Lys Leu Ser Arg Ala Arg Asp Leu Gln Asp Pro Gly Ser Arg Leu Gly
1               5                  10                  15

(2) INFORMATION FOR SEQ ID NO:13:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Ser Phe Arg Glu Leu Glu Ile Cys Arg Ile Pro Gly Leu Asp
1               5                  10

(2) INFORMATION FOR SEQ ID NO:14:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Ala Phe Ala Ser Ser Arg Ser Ala Gly Ser Arg Val
1               5                  10

(2) INFORMATION FOR SEQ ID NO:15:

(i) SEQUENCE CHARACTERISTICS:
        (A) LENGTH: 16 base pairs
        (B) TYPE: nucleic acid
        (C) STRANDEDNESS: single
```

(D) TOPOLOGY: linear (ii) MOLECULE TYPE: other nucleic acid
        (A) DESCRIPTION: /desc = "Synthetic Linker"

(xi) SEQUENCE DESCRIPTION: SEQ ID NO:15:

GATCGCCATC GATGGC                                                           16

(2) INFORMATION FOR SEQ ID NO:16:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Linker"

(xi) SEQUENCE DESCRIPTION: SEQ ID NO:16:

GATCGCCATC GATGGC                                                           16

(2) INFORMATION FOR SEQ ID NO:17:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CTAGTGCTAT AAT                                                              13

(2) INFORMATION FOR SEQ ID NO:18:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 157..570

(xi) SEQUENCE DESCRIPTION: SEQ ID NO:18:

GGAGCTTTTT TGTTTTGGGC AACTTGTTTT CTTCGTAATT TCTGTCAGTG GCTGATGATT     60

AAATGTTTTA CTTTTCATTG CTCTAATCAG CTTCTCATAG GCAAATCAAA TAAAGTCTGA    120

TATAACACTC AATAGCAAAC ATCGGAGGTA GATAGA ATG CAA AAC TTA GAT TTA      174
                                        Met Gln Asn Leu Asp Leu
                                         1               5

ATC GAA AAT GAA ATC AAA ACA GTA ATT GAT ACT TGT GAC AAG TTA ATC      222
Ile Glu Asn Glu Ile Lys Thr Val Ile Asp Thr Cys Asp Lys Leu Ile
            10                  15                  20

CAT CAA GAA AAA TTT GAT GAA TTG GTT AAC TTT TAT ACT GAA GAT GCC      270
His Gln Glu Lys Phe Asp Glu Leu Val Asn Phe Tyr Thr Glu Asp Ala
        25                  30                  35

GTT TTA GTT ATT AAA CCT GGC ATG CTC GCG AAT GGA CGA GAA CAA ATT      318
Val Leu Val Ile Lys Pro Gly Met Leu Ala Asn Gly Arg Glu Gln Ile
    40                  45                  50

AAA TCA GCT TTT ATA AAA ATT GCA TCT TAC TTT GAT AAT TCT ATT AAA      366
Lys Ser Ala Phe Ile Lys Ile Ala Ser Tyr Phe Asp Asn Ser Ile Lys

-continued

```
            55                    60                   65                    70
CCT CTT GAA GGA AAA ATG GTT TAT CTT CTT GCT GGT GAT ACC GTT CTT        414
Pro Leu Glu Gly Lys Met Val Tyr Leu Leu Ala Gly Asp Thr Val Leu
                    75                   80                   85

GTT TTG GCT CAA ACT TTT ATT GAA GCA AAC CAA TCA GCA ACT GCT CAG        462
Val Leu Ala Gln Thr Phe Ile Glu Ala Asn Gln Ser Ala Thr Ala Gln
            90                  95                  100

TCT GAA TTT TCA ATG GAG AGA AGA GCA ACT TAT GTT TTT CGC AAC ATA        510
Ser Glu Phe Ser Met Glu Arg Arg Ala Thr Tyr Val Phe Arg Asn Ile
        105                 110                 115

GAT GGA AAA TGG TTA TGT GCA ATT GAT AAT TCT TAT GGG ACA ACT CTT        558
Asp Gly Lys Trp Leu Cys Ala Ile Asp Asn Ser Tyr Gly Thr Thr Leu
    120                 125                 130

ATT GAC GAA AAA TAAAATAGAA AGCTATACTT ACAACTTCAT TGAGGTTGTT            610
Ile Asp Glu Lys
135

TTTTACTTTA ATTATTATTT ATTTTATCTG TTTATTCTTC CTTTTTCATC CCTAGGCATT      670

TTTTTACATC TTACTTCAAT TTTAAA                                          696
```

(2) INFORMATION FOR SEQ ID NO:19:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:19:

```
Met Gln Asn Leu Asp Leu Ile Glu Asn Glu Ile Lys Thr Val Ile Asp
  1               5                  10                  15

Thr Cys Asp Lys Leu Ile His Gln Glu Lys Phe Asp Glu Leu Val Asn
             20                  25                  30

Phe Tyr Thr Glu Asp Ala Val Leu Val Ile Lys Pro Gly Met Leu Ala
         35                  40                  45

Asn Gly Arg Glu Gln Ile Lys Ser Ala Phe Ile Lys Ile Ala Ser Tyr
 50                  55                  60

Phe Asp Asn Ser Ile Lys Pro Leu Glu Gly Lys Met Val Tyr Leu Leu
 65                  70                  75                  80

Ala Gly Asp Thr Val Leu Val Leu Ala Gln Thr Phe Ile Glu Ala Asn
             85                  90                  95

Gln Ser Ala Thr Ala Gln Ser Glu Phe Ser Met Glu Arg Arg Ala Thr
            100                 105                 110

Tyr Val Phe Arg Asn Ile Asp Gly Lys Trp Leu Cys Ala Ile Asp Asn
        115                 120                 125

Ser Tyr Gly Thr Thr Leu Ile Asp Glu Lys
    130                 135
```

(2) INFORMATION FOR SEQ ID NO:20:

(i) SEQUENCE CHARACTERISTICS:
        (A) LENGTH: 129 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:20:

Met Glu Gln Gln Leu Lys Asp Ile Ile Ser Ala Cys Asp Leu Ala Ile

```
1               5                  10                 15
Gln Asn Glu Asp Phe Asp Thr Leu Met Asn Tyr Tyr Ser Glu Asp Ala
                20                 25             30
Val Leu Val Val Lys Pro Gly Met Ile Ala Arg Gly Lys Glu Glu Ile
         35                  40                 45
Lys Lys Ala Phe Ile Thr Ile Ala Asn Tyr Phe Asn His His Ile Val
     50                  55                 60
Pro Thr Gln Gly Lys Met Ile Leu Leu Glu Ala Gly Asp Thr Val Leu
 65                  70                 75                  80
Val Leu Ser Gln Thr Leu Leu Asp Ser Asp Lys Lys Asp Ser Glu Tyr
                 85                 90                 95
Ala Met Glu Arg Arg Ala Thr Tyr Val Phe Lys Lys Asn Ala Gln Gly
                100                 105                110
Glu Trp Leu Cys Val Ile Asp Asn Ser Tyr Gly Thr Asp Leu Ile Gly
            115                120                 125
Val
```

(2) INFORMATION FOR SEQ ID NO:21:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:21:

TTTCTGCTGC AGCCCCGTTG TCAGGTGTTT ACGCTGCGCC AAGACCTAC TGCGAG    56

(2) INFORMATION FOR SEQ ID NO:22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:22:

ACGCGTCGAC CTAGGCCAGC ATCGAGTC    28

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:23:

GGAAGATCTA TGACAGAGCA GCAGTGG    27

(2) INFORMATION FOR SEQ ID NO:24:

(i) SEQUENCE CHARACTERISTICS:
        (A) LENGTH: 25 base pairs
        (B) TYPE: nucleic acid (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO:24:

ACGCGTCGAC CTATGCGAAC ATCCC                                              25

(2) INFORMATION FOR SEQ ID NO:25:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO:25:

GGAAGATCTT GCGAACATCC CAGTG                                              25

(2) INFORMATION FOR SEQ ID NO:26:

(i) SEQUENCE CHARACTERISTICS:
            (A) LENGTH: 170 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:26:

ATTTTTGGTT GCCATTTGTT AACGCTGCCT CCTCTCCCTA GTGCTATAAT AAAAATGGCC        60

AAAAAAAAAC CATTTTATTG ACTATATTTG CAATTTATTT ACACATTATC TTTTCAGAAC       120

CAAAATCTGG CCCATTTTGG AACAGACTTC TACTATTTTG TTGTCTAGTA                  170

(2) INFORMATION FOR SEQ ID NO:27:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:27:

TAATTTATTT ACACATTATC T                                                  21

(2) INFORMATION FOR SEQ ID NO:28:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:28:

TAATTTATTT ATACATTATC T                                                  21

(2) INFORMATION FOR SEQ ID NO:29:

(i) SEQUENCE CHARACTERISTICS:

-continued

```
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CAATTTATTT ATACATTATT T                                              21

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CAATTTATTT ACACATTATT T                                              21
```

LACTIC ACID BACTERIAL REGULATABLE EXPRESSION SYSTEM

This application is a 35 U.S.C. §371 national phase application of PCT/DK97/00341 filed Aug. 22, 1999, which is a continuation-in-part of application Ser. No. 08/711,434, filed Sep. 6, 1996 now abandoned.

FIELD OF INVENTION

The present invention provides novel lactic acid bacterial regulatable expression systems which are based on modification of naturally occurring regulatory sequences whereby the expression of genes can be modulated to obtain production of gene products at desirable levels. Recombinant lactic acid bacteria comprising such expression systems are useful in the manufacturing of food products, in the production of animal feed or as production strains in the manufacturing of homologous or heterologous gene products, including pharmaceutically or immunologically active gene products. Recombinant lactic acid bacteria expressing antigenic determinants as provided herein are useful as live vaccines.

TECHNICAL BACKGROUND AND PRIOR ART

For centuries, starter cultures of lactic acid bacteria have been used in food production due to their ability to convert sugars by fermentation into organic acids, predominantly lactic acid, and various metabolites associated with the development in the fermented food products of a desirable taste and flavour. Several lactic acid bacteria inherently produce hydrolytic enzymes including peptidases, proteases and lipolytic enzymes, the production of which may e.g. contribute to a desired flavour development in cheeses.

However, for industrial production of a wide range of fermented food products such as all the well-known traditional dairy products including yoghurt, acidophilus milk, butter and cheeses; fermented vegetables; fermented meat products and animal feed, a large range of lactic acid bacterial starter cultures, each being adapted to particular types of food products, are required. Such cultures are presently being selected from naturally occurring strains of lactic acid bacteria on the basis of characteristics such as their ability to ferment sugars present in the food product to be fermented, specific growth temperature requirements, production of desired flavouring compounds, the specific combination of which characteristics renders a specifically selected wildtype culture useful for the production of a particular food product but normally less useful for the production of others.

Obviously, this presently used procedure for developing useful lactic acid bacterial cultures by selection of naturally occurring strains is cumbersome and costly. Furthermore, it has proven difficult to provide starter culture strains which combine all of the required characteristics at an optimal level. Presently, this problem is usually solved by the use of starter cultures comprising a multiplicity of selected lactic acid bacterial strains each having one or several of the characteristics desirable for a particular food product. The necessity to use such mixed cultures will of course add to the costs in the manufacture of lactic acid bacterial starter cultures.

Based on their traditional and long term application in food manufacturing and the fact that they are considered as nonpathogenic, the lactic acid bacteria are generally recognized as safe (GRAS) food ingredients, even if they are present in a fermented food product as live bacteria at a very high number, such as $10^8$ to $10^9$ per g.

Currently, it is widely recognized that a substantial industrial need exists to find economically and technically more feasible ways of developing improved lactic acid bacteria for use as food or feed starter cultures or for the production of desired gene products including providing lactic acid bacteria which are useful for a wide range of applications. It is evident that recombinant DNA technology may provide the means to meet this need. In this context, it is crucial that lactic acid bacteria for food manufacturing which are developed by introduction of desired genes by use of gene technology can still be recognized as safe for consumption. It is therefore considered by the food industry that it is essential that recombinant lactic acid bacteria essentially contain only DNA of lactic acid bacterial origin including DNA from wildtype extrachromosomal plasmids frequently found in starter culture strains or non-lactic acid bacterial DNA which does not confer to the recombinant strains any hazardous phenotypic traits.

There have been several attempts of providing genetically improved lactic acid bacteria. Most of these attempts have been directed to the construction of recombinant expression vectors coding for desired gene products and capable of replicating in lactic acid bacteria. However, very few of these attempts have resulted in vectors comprising only lactic acid bacterial DNA.

In addition to their use as food starter cultures, lactic acid bacteria can be used as production strains for the manufacturing of desired biologically functional gene products such as pharmaceutically and immunologically active compounds.

As mentioned above, the present invention provides novel lactic acid bacterial regulatable gene expression systems which are based on modification of naturally occurring regulatory sequences which are operably associated or linked with a gene, whereby the expression of the gene can be altered significantly.

Inducible or regulatable gene expression systems are highly important for expression of genes encoding proteins that are either (i) toxic to the host organism, (ii) needed in large quantities, (iii) used to study the effect of particular gene functions on cellular metabolism or regulation or (iv) produced at a particular point in time or under particular environmental conditions. Whereas inducible expression systems have been developed for use in *E. coli,* only a few inducible expression systems for use in lactic acid bacteria have been described.

An example of a lactic acid bacterial inducible expression system is a system based on the lac promoter transcribing the lac genes of *Lactococcus lactis*. The lac promoter can be repressed by the LacR repressor and a six-fold induction of transcription can be obtained by replacing glucose in the growth medium with lactose (van Rooijen et al., 1992). This naturally occurring expression system has been combined with the T7 RNA polymerase/T7 promoter system from *E. coli* (Wells et al., 1993a,b; Steidler et al., 1995). The lac promoter controls the expression of T7 RNA polymerase, which recognizes the T7 promoter, allowing inducible expression of genes cloned downstream of the T7 promoter. This system has been used to produce tetanus toxin fragment C and murine interleukin-2.

Another example is the use of the dnaJ promoter transcribing the dnaJ gene of *L. lactis,* which has been used to generate inducible expression of a heterologous protein after heat shock induction (van Asseldonk et al., 1993). Increasing the temperature from 30° C. to 42° C. resulted in about four-fold induction of gene transcription.

Other examples of lactic acid bacterial inducible expression systems include the use of phage specific expression signals from lytic bacteriophages of *L. lactis* which can be applied to express heterologous genes upon phage infection (O'Sullivan et al., 1996), and systems based on induction of gene expression by supplementing the bacterial growth medium with an inducer substance such as the toxic antitumour antibiotic Mitomycin C (Nauta et al., 1996) or a bacteriocin such as nisin (Ruyter et al., 1996, EP 0712 935 A2).

Accordingly, all the known methods of controlling gene expression in lactic acid bacteria are based upon the addition to the growth medium of inducing compounds or bacteriophages, or on temperature shifts, i.e. exogenously added factors which may not be acceptable according to regulatory safety requirements or which are not economically or industrially feasible in the context of industrial use of lactic acid bacteria in food or feed manufacturing or in the manufacturing of desired gene products.

It has recently been discovered that it is possible to isolate lactic acid bacterial promoters which are inducible or regulatable by the presence/absence or the concentration of one or more environmental factors associated with conventional lactic acid bacterial industrial production methods such as pH, growth temperature, composition of the growth medium including the ionic strength/NaCl content, the presence/absence of purine nucleotide precursors and/or the growth phase/growth rate of the bacterium (WO 94/16086, Israelsen et al., 1995).

It is evident that regulatable expression systems based on such environmental or growth condition factors as mentioned above, and which are normally present in industrial culture media for lactic acid bacteria either initially or during the culturing, will represent a highly attractive approach for regulating the production of homologous or heterologous gene products in lactic acid bacteria. However, in order for the application of these regulatable expression systems to be successful, the selected promoter must be effective and lead to the production of a desired protein in sufficiently high amounts under industrial conditions to facilitate an economically viable production or manufacturing process. However, it has been found that such otherwise useful naturally occurring regulatable lactic acid bacterial promoters may only have a relatively weak promoter activity.

It has now been discovered that the activity of such naturally occurring inducible or regulatable lactic acid bacterial promoters can be increased by modifying the nucleotide region in which the promoter is located and, most importantly, that such an increased promoter activity can be obtained without reducing or eliminating the inducibility by the above mentioned growth condition factors. The invention has also made it possible to provide sets or panels comprising lactic acid bacteria producing a desired gene product at different levels under the same conditions. Additionally, it has also been found that the modification of the promoter region sequences may result in strains having a modulated expression level under induced conditions as compared to the regulation by the corresponding non-modified promoter region.

SUMMARY OF THE INVENTION

Accordingly, in a first aspect, the present invention relates to an expression vector capable of being replicated in a lactic acid bacterial cell, said vector comprising
(i) a promoter region comprising (a) a promoter sequence element the function of which is regulatable by a factor selected from the group at least consisting of pH, the growth temperature, the oxygen content, a temperature shift eliciting the expression of heat chock genes, the composition of the growth medium including the ionic strength/NaCl content, the presence/absence of essential cell constituents or precursors herefor, and the growth phase of the bacterium, the growth rate of the bacterium and (b) at least one further nucleotide sequence element, the position, orientation, presence and/or sequence of which element has a regulatory effect on the expression of a gene operably linked to the promoter region, and
(ii) at least one restriction site,
the position, orientation, presence and/or sequence of at least one of said elements (a) or (b) being modified relative to the position, orientation, presence and/or sequence of the corresponding non-modified element.

In further aspects of the invention there is provided a lactic acid bacterium which is transformed with a vector as defined above, and a recombinant lactic acid bacterial cell comprising the following operably interlinked elements, the position, orientation, presence and/or sequence of at least one of said elements having a regulatory effect on the expression of the gene:
(i) a gene coding for a desired gene product which is expressible in a lactic acid bacterium,
(ii) a promoter sequence element the function of which is regulatable by a factor selected from the group at least consisting of pH, the growth temperature, the oxygen content, a temperature shift eliciting the expression of heat chock genes, the composition of the growth medium including the ionic strength/NaCl content, the presence/absence of essential cell constituents or precursors herefor, and the growth phase/growth rate of the bacterium, and
(iii) at least one further nucleotide sequence element,
the position, orientation, presence and/or sequence of at least one of said elements being modified relative to the position, orientation, presence and/or sequence of the non-modified element whereby the level at which the gene is expressed is altered.

In a still further aspect the invention pertains to a lactic acid bacterial starter culture comprising any of the above cells.

There is also provided a method of producing a food product comprising adding to the food product starting materials a lactic acid bacterial starter culture according to the invention and a method of producing an animal feed comprising adding to the feed components a lactic acid bacterial starter culture as defined above.

In still further aspects, the invention relates to a method of producing a pharmaceutically active gene product, the method comprising cultivating any of the above lactic acid bacterial cells according to the invention which cells comprise a gene coding for the pharmaceutically active gene product under conditions where the gene is expressed, and isolating the gene product and to a method of producing an immunologically active gene product, the method comprising cultivating a lactic acid bacterial cell which comprises a gene coding for the immunologically active gene product under conditions where the gene is expressed, and isolating the gene product.

Specifically, there is provided a method of producing polypeptides derived from a Mycobacterium species such as *M. tuberculosis*.

DETAILED DISCLOSURE OF THE INVENTION

One primary object of the present invention is to provide a lactic acid bacterium in which the expression of desired genes under the control of a promoter region comprising at least one regulatory sequence or signal is inducible and/or regulatable by one or more environmental or growth condition factors and is altered by modifying the regulatory sequence or signal.

As used herein the term "lactic acid bacterium" designates a gram-positive, microaerophilic or anaerobic bacterium which ferments sugars with the production of acids including lactic acid as the predominantly produced acid, acetic acid and propionic acid. The industrially most useful lactic acid bacteria are found among Lactococcus spp., Streptococcus spp., Lactobacillus spp., Leuconostoc spp., Pediococcus spp., Brevibacterium spp. and Propionibacterium spp. Additionally, lactic acid producing bacteria belonging to the group of the strict anaerobic bacteria, bifidobacteria, i.e. Bifidobacterium spp. which are frequently used as food starter cultures alone or in combination with lactic acid bacteria, are generally included in the group of lactic acid bacteria.

The expression vector according to the invention comprises in its promoter region a promoter sequence element, the activity or function of which is inducible and/or regulatable by the presence/absence or the concentration of one or more environmental or growth condition factors associated with conventional lactic acid bacterial industrial production methods. In the present context, the expression "promoter sequence" is used in the conventional sense to designate the site whereto RNA polymerase can be bound.

The promoter region may, in accordance with the invention be derived from any bacterial cell, but in preferred embodiments it is derived from a lactic acid bacterial species including the above species and Bifidobacterium spp. In useful embodiments, the promoter region is derived from a promoter region of *Lactococcus lactis* including *Lactococcus lactis* subspecies *lactis*, e.g the strain designated MG1363 [this strain is also referred to in the literature as *Lactococcus lactis* subspecies *cremoris* (Nauta et al., 1996)], and *Lactococcus lactis* subspecies *lactis* biovar. *diacetylactis*. A naturally occurring inducible promoter region which can be modified in accordance with the invention may be isolated by any conventional methods for identifying and isolating nucleotide sequences comprising a promoter sequence and sequences having an effect on the activity of the promoter. Examples of such promoter regions which, in accordance with the present invention, are useful as starting materials are given in WO 94/16086 including a region comprising the promoter P170. Typically, such a promoter region starter material has a size which is in the range of 50 to 10,000 base pairs, such as in the range of 50 to 2000 base pairs including a range of 50 to 200 base pairs.

Preferably, the above environmental or growth condition factors are selected from pH, the growth temperature, the oxygen content, a temperature shift eliciting the expression of heat chock genes, the composition of the growth medium including the ionic strength/NaCl content, the presence/absence of essential cell constituents or precursors herefor, the growth phase of the bacterium or the growth rate of the bacterium.

It will be understood that when the promoter is one, the induction or regulation of which is controlled by one or more substances present in a conventional growth medium, substances which are not normally components of such media, such as antibiotics or bacteriocins are, in accordance with the invention, generally not included as environmental or growth condition factors.

The promoter region of the vector according to the invention comprises, as it is mentioned above, at least one further nucleotide sequence element, the position, orientation, presence and/or sequence of which element has a regulatory effect on the expression of a gene operably linked to the promoter region. As used herein, the expression "further nucleotide sequence" may include a sequence encoding a ribosome binding site, a transcription factor binding site, a repressor binding site, a site mediating attenuated or auto-regulated gene expression, a DNA sequence which can be transcribed into MRNA having an altered affinity for the ribosome or an altered affinity for nucleases, a DNA sequence comprising a transcription terminus, or any other sequence capable of modulating and/or enhancing gene expression. In the present context, this term will also include DNA sequences in the promoter region which has no specifically recognized function, such as e.g. sequences located between or adjacent to −10 and −35 promoter sequences and other consensus sequences.

In accordance with the invention, the position, orientation, presence and/or sequence of at least one of said promoter sequences and further nucleotide sequence elements of the expression vector is modified relative to the position, orientation, presence and/or sequence of its corresponding non-modified element.

Thus, contemplated modifications of the sequences of the promoter region include any modification hereof which affects the frequency of transcription initiation. This is obtained by substitution, deletion and/or insertion of one or more nucleotides using any conventional technique for that purpose including random or site-directed mutagenesis to provide e.g. point mutations e.g. by using PCR or a transposable element.

Further modifications of the promoter region may, in accordance with the invention, also be made in one or more of the above further nucleotide sequences using any of the above techniques, such as it will be explained in details in the following examples.

It will be understood that it is possible to provide an expression vector according to the invention wherein both a promoter sequence and a further nucleotide sequence is modified.

In one preferred embodiment, the vector according to the invention is one wherein the modification of at least one of the above elements results in that the expression of a gene which is operably linked to the promoter region is altered relative to the expression of the same gene under the control of the non-modified promoter region. In the present context, the expression "altered expression" is used to indicate that the amount of the gene product being produced is different from the amount of gene product produced when using, under essentially identical environmental or growth conditions, a bacterium comprising the same gene under the control of a corresponding non-modified promoter region from which the modified promoter region is derived.

In one preferred embodiment, the above modification of a promoter sequence element and/or a further nucleotide sequence element results in the expression of the gene which is under the control of the modified promoter region being enhanced, resulting in an increased amount of gene product being produced as compared to the amount being produced by a bacterium in which the same gene is under the control of the non-modified promoter region from which the modified promoter region is derived. Preferably, the production of the gene product is increased at least two-fold, more preferably at least three-fold, even more preferably at least four-fold. Even substantially higher increases can be obtained such as at least five-fold, more preferably at least ten-fold and even more preferably at least fifty-fold including at least hundred-fold such as at least two hundred-fold increase.

The expression vector according to the invention comprises at least one restriction site for the insertion of useful nucleotide sequences including a gene coding for a desired gene product so as to have the expression of the gene under the control of the modified promoter region, i.e. the gene is inserted so that it is operably linked to the promoter region. The gene as defined above may be a homologous or a heterologous gene including a gene derived from a different lactic acid bacterium. It may be advantageous that the gene product as expressed by the inserted gene is translocated to the outside of the cell membrane or even released into the cultivation medium. This requires that the gene is preceded by a nucleotide sequence encoding a signal peptide functionality or that the gene is part of a hybrid sequence coding for a fusion protein which is secretable as the result of the fusion partner being provided with a leader sequence. Accordingly, the gene which is inserted into a vector according to the invention may, if required, comprise such a nucleotide sequence coding for a signal peptide, i.e. a signal sequence. The signal peptide may be functionally linked to a propeptide.

In useful embodiments, the thus inserted gene coding for a desired gene product is selected from a gene coding for a lipase, a gene coding for a peptidase, a gene coding for a protease, a gene coding for a nuclease, a gene coding for a gene product involved in carbohydrate metabolism, a gene coding for a gene product involved in citrate metabolism, a gene coding for a gene product involved in bacteriophage resistance, a gene coding for a lytic enzyme, a gene coding for a viral protein such as a capsid protein, a microbial cell surface protein and a gene coding for a bacteriocin. The gene may also be one which codes for a gene product conferring resistance to an antibiotic or a bacteriocin such as e.g. nisin or pediocin.

In specific embodiments, the vector comprises a gene coding for a β-galactosidase. Examples of such vectors include the plasmids pAMJ553, pAMJ567 and pAMJ586 which were deposited on 4 September 1996 with the Deutsche Sammlung von Mikroorganismen und Zellkulturen GmbH (DSM), Mascheroder Weg 1b, D-38124 Braunschweig, Germany under the accession numbers DSM 11135, DSM 11136 and DSM 11137, respectively. These three vectors which contain the same β-galactosidase gene express the gene product hereof at different levels under the same environmental or growth conditions due to different modifications of the promoter region as it described in Example 6 and accordingly, they represent an example of a set of expression vectors wherein a gene is expressed at different levels. Other examples of such a set of vectors include the vectors pSMA607, pSMA609 and pSMA610 as described in Example 7 which are provided with a signal peptide, and the vectors pSMA604, pSMA605 and pSMA606 which correspond to the above vectors pSMA607, pSMA609 and pSMA610 except that they lack the signal peptide.

In particularly interesting embodiments, the vector comprises a gene coding for a biologically functional gene product including an enzyme which regulates the formation of flavouring compounds, a toxin, an immunologically active polypeptide, a pharmaceutically active polypeptide, and an antimicrobially active polypeptide. In this connection, interesting enzymes which directly or indirectly regulate the formation of flavouring (aroma) compounds in lactic acid bacteria such as acetaldehyde, acetoin, 2,3 butylene glycol and diacetyl include as examples pyruvate formate lyase, alcohol dehydrogenase, pyruvate decarboxylase, α-acetolactate synthetase, lactate dehydrogenase and acetaldehyde dehydrogenase.

Immunologically active gene products include any sequences which comprise at least one epitope. Such sequences may be useful as vaccines and/or diagnostic agents, and can be derived from any pathogenic organism against which there is a need to immunize an animal such as a mammal including a human being. It will be understood that the epitope expressed by the inserted gene can be one which is secreted out of the cell into the culture medium or it can be located on the outer surface of the host organism whereby it will be possible to apply the host cell itself as a vaccine. Alternatively, the epitope can be produced intracellularly, in which case it is isolated from the cell. Another interesting means of having an epitope expressed is by inserting the nucleotide sequence coding for the epitope into the gene being inserted into the vector such that the epitope in an immunologically active form is expressed as part of a fusion protein.

In a specific embodiment, the vector according to the invention comprises a sequence coding for a mycobacterial antigenic determinant or epitope, i.e. an immunologically active oligo- or polypeptide which has, when administered to an animal including a human being, a stimulating effect on the humoral and/or cellular immune response.

In particular, such a coding sequence may be derived from an organism that belongs to the group of Mycobacterium species which is generally referred to as the "tuberculosis complex" that includes *Mycobacterium tuberculosis, M. bovis* and *M. africanum*. Such antigenic gene products of mycobacterial origin have potential use as tuberculosis vaccines and/or as diagnostic reagents in the tuberculosis skin test. It is evident that industrial production of vaccines and diagnostically active agents for human and animal use in a safe, non-pathogenic organism as a lactic acid bacterium will be highly advantageous. As it is described in the following examples, the present invention has made it possible to use lactic acid bacteria transformed with the vector according to invention as production strains for the manufacturing of mycobacterial polypeptides including polypeptides carrying epitopes.

It has thus been found that mycobacterial polypeptides can be produced by a lactic acid bacterium according to the invention which secretes the polypeptides into the culture medium in an amount which is at least 30 mg/l and higher yields are contemplated such as at least 50 mg/l or at least 100 mg/l, e.g. at least 500 mg/l including a yield of at least 1000 mg/l. In addition to modulating the expression of the mycobacterial polypeptide in accordance with the invention to obtain a higher level of expression, an increased yield of these antigens can be obtained by inserting the coding sequence in 2 or more copies.

In further useful embodiments, the gene inserted into the vector is one coding for an antibody including a monoclonal and a polyclonal antibody. Such a gene can be derived from any animal source including birds, mammals and human beings.

In addition to the above sequences which form part of the expression vector according to the invention, the vector may also comprise a selectable marker allowing e.g. the stable maintenance of the vector in a host cell. The choice of a suitable marker will depend on the particular use of the vector and the choice can readily be made by those skilled in the art. Examples of useful selectable markers include auxotrophy markers being complementable or genes mediating resistance to antibiotics or bacteriocins.

In accordance with the invention there is, in a further aspect hereof, provided a recombinant lactic acid bacterium which is transformed with a vector as described above. In useful embodiments, the vector is contained in a plasmid which can replicate in a lactic acid bacterium or, if preferred, the vector or separate elements hereof may be integrated into the chromosome of the host cell, e.g. by use of a Campbell-like integration technique where a vector comprises at least one nucleotide sequence element which is homologous to a chromosomally encoded nucleotide sequence, thereby facilitating the integration of the vector into the chromosome by a recombination event involving homologous sequences. It is also possible to construct a recombinant lactic acid bacterium in which at least one further recombinational event has occurred, including a recombination event leading to the excision of chromosomal DNA sequences.

A recombinant lactic acid bacterium as defined above may be one which is selected from Lactococcus spp. including *Lactococcus lactis* spp. *lactis, Lactococcus lactis* spp. *diacetylactis* and *Lactococcus lactis* spp. *cremoris,* Streptococcus spp. including *Streptococcus salivarius* spp. *thermophilus,* Lactobacillus spp. including *Lactobacillus acidophilus, Lactobacillus plantarum, Lactobacillus delbrückii* spp. *bulgaricus, Lactobacillus helveticus,* Leuconostoc spp. including *Leuconostoc oenos,* Pediococcus spp., Brevibacterium spp., Propionibacterium spp. and Rifidobacterium spp. including *Bifidobacterium bifidum.*

In a still further aspect, the invention pertains to a recombinant lactic acid bacterial cell comprising as operably interlinked elements, the position, orientation, presence and/or sequence of at least one of these having a regulatory effect on the expression of a gene of the cell coding for a desired gene product: (i) the gene coding for a desired gene product, (ii) a promoter sequence element, the function of which is inducible or regulatable by an environmental or growth condition factor as defined above, and (iii) at least one further nucleotide sequence element, the position, orientation, presence and/or sequence of at least one of said elements being modified relative to the position, orientation, presence and/or sequence of the non-modified element whereby the level at which the gene is expressed is altered. The methods of modifying any of these elements are the same as those described above for corresponding sequences of the expression vector according to the invention.

It will be understood that each of the above operably interlinked elements may be located on the same or on different replicons of the cell, the term "replicon" including a chromosome, a plasmid and a bacteriophage.

The lactic acid bacterium may be selected from any of the above lactic acid bacterial species.

A recombinant lactic acid bacterium as provided herein may be useful in starter cultures for the manufacturing of food products including dairy products, meat products and vegetable products and in the preservation of animal feed. In the latter context, the present recombinant bacteria are particularly interesting as inoculants in field crops which are to be ensiled. When the bacteria are to be used for these purposes they may conveniently be provided in the form of dried or frozen bacterial concentrates e.g. containing $10^{10}$ to $10^{12}$ colony forming units (CFUs) per g of concentrate. Such concentrates are typically provided in the form of freeze-dried or frozen starter culture compositions comprising in addition to the lactic acid bacteria, additives which contribute to obtaining a high concentration of viable cell and a desired shelf life of the composition, including cryoprotectants, or additives which support rapid activity of the cells of the composition when added to the material to be fermented such as nutrients or buffering agents.

It is an interesting aspect of the invention that food starter cultures may be provided which are modified in accordance with the invention such that one or more of the sugar and/or citrate metabolic pathways of the cells in the culture have been modified by modifying the expression of genes which directly or indirectly control the formation of desirable flavouring compounds such as diacetyl, acetaldehyde or 2,3 butylene glycol.

The starter culture according to invention may, if desired, comprise a mixture of separate strains of lactic acid bacteria as defined herein. Such a mixture of strains may comprise individual strains in which a desired gene, which is under the control of differently modified promoter regions derived from the same naturally occurring promoter region, is expressed at different levels under the same conditions. Alternatively, the mixture of strains may comprise a set or panel of strains in which the expression of the desired gene is under the control of modified promoter regions originating from different naturally occurring promoter regions which respond differently to inducing or regulating environmental or growth condition factors. Alternatively, a mixed culture of lactic acid bacteria according to the invention may comprise different genes encoding different gene products.

A further interesting use of a recombinant lactic acid bacterium as defined herein is in the manufacturing of a probiotically active composition. The term "probiotically active" indicates that the bacteria selected for this purpose have characteristics which enable them to colonize in the gastrointestinal tract and hereby exert a positive regulatory effect on the microbial flora in this habitat. Such effect may be recognizable as an improved food or feed conversion in human or animals to which the bacteria are administered, or as an increased resistance against invading pathogenic micro-organisms.

Furthermore, it is contemplated that the present recombinant lactic acid bacteria may be useful as production strains in industrial production of a wide range of desired gene products such as those mentioned above.

The lactic acid bacterial starter culture according to the invention is useful in methods of producing a food product as mentioned above. The starter culture can be used in accordance with conventional methods of producing food products which include a step of acidifying or fermenting the starting materials for the food product by using a lactic acid bacterium.

The lactic acid bacterial starter culture as provided herein may also be useful in starter cultures for the preservation of animal feed. In the latter context, the starter cultures are particularly interesting as inoculants which are added to field crops such as grass or maize to be ensiled.

A further interesting use of the modified lactic acid bacteria according to the invention is as production strains in the manufacturing of desirable gene products including pharmaceutically active gene products. Accordingly, there is, as it is mentioned above, provided a method of producing a pharmaceutically active gene product which method comprises the steps of cultivating a lactic acid bacterial cell according to the invention which cell comprises a gene coding for the pharmaceutically active gene product under conditions where the gene is expressed, and isolating the gene product.

Genes which are to be expressed in the above recombinant lactic acid bacteria can be isolated from any animal source including mammals, human beings, birds or fish. As typical examples of interesting gene products in this connection can be mentioned proteases, protease activators and inhibitors, cytokines, enzymes or peptide hormones, although it will be understood that any gene product having a pharmaceutical activity is encompassed by the present invention.

A particularly interesting class of gene products which can be produced in accordance with the invention comprises immunologically active gene products. Accordingly, the invention provides, as it is mentioned above, in one aspect a method of producing such an immunologically active product, using as the production cell a lactic acid bacterial cell according to invention. In this context, the expression "immunologically active gene product" includes an antigen, an epitope, a polypeptide comprising an epitope, an antibody such as a monoclonal antibody, and fragments and/or derivatives hereof. It is also contemplated that biologically active substances which can modulate or stimulate the immune system can be produced according to the present method In specific embodiments, the immunologically active gene product is an oligo- or polypeptide derived from a pathogenic bacterial or viral species such as a gene product derived from a Mycobacterium species as it described in the following examples. Specific examples include peptides which are generally referred to in the art as short-term culture filtrate peptides from *M. tuberculosis* such as the MPT64 antigen (Oettinger et al., 1995) or the ESAT-6 polypeptide (Sorensen et al., 1995).

The immunologically active compounds produced according to the invention can be further processed into e.g. vaccine compositions, therapeutic agents, diagnostic or prognostic agents in accordance with methods which are well-known in the respective fields.

Figure 2:
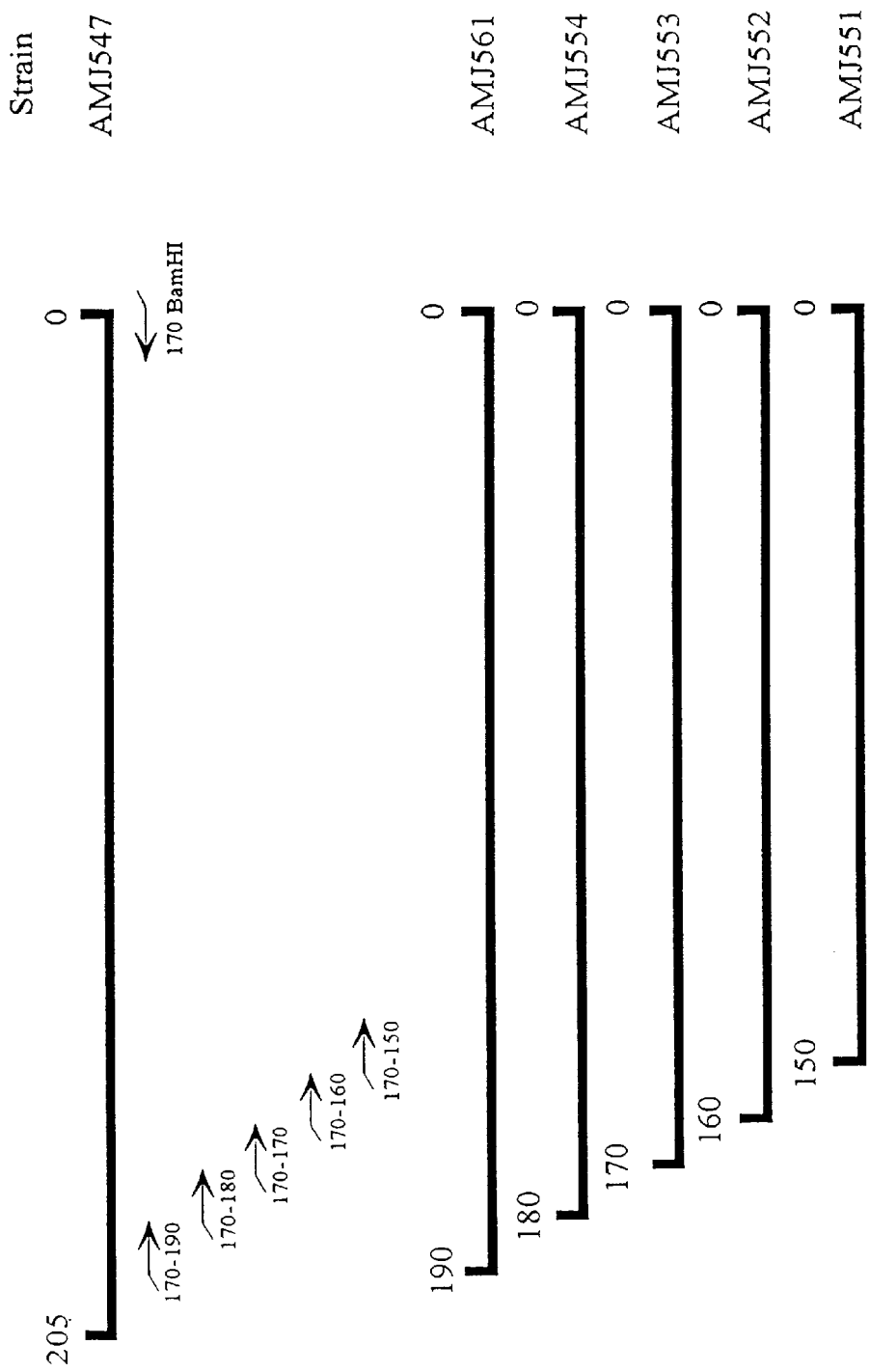
Figure 3:
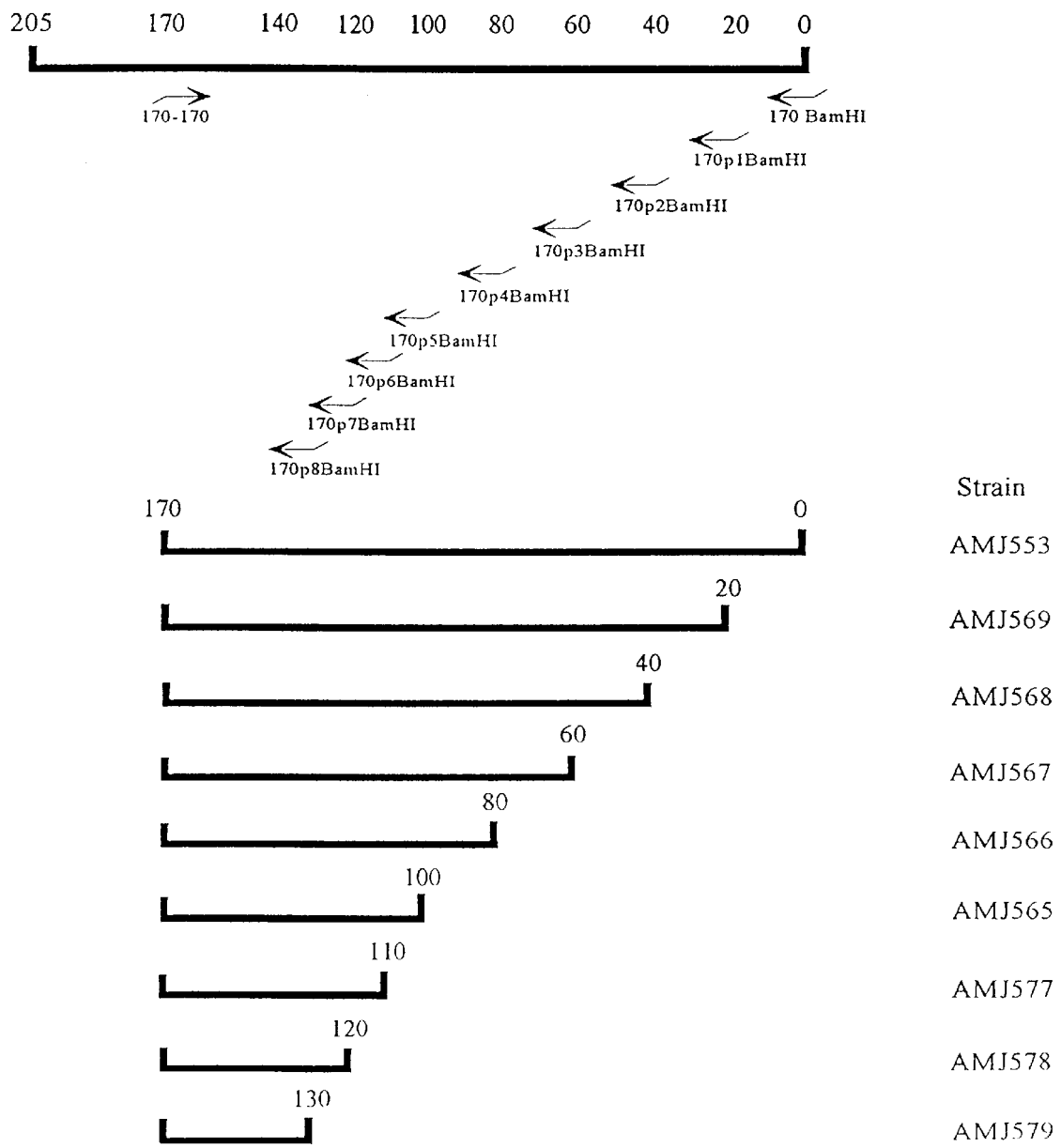
Figure 4:
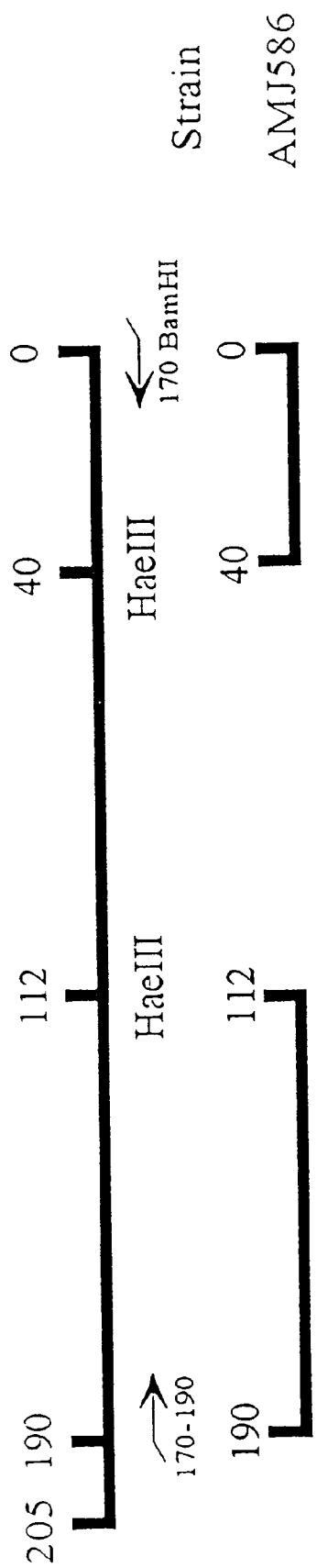
Figure 5:
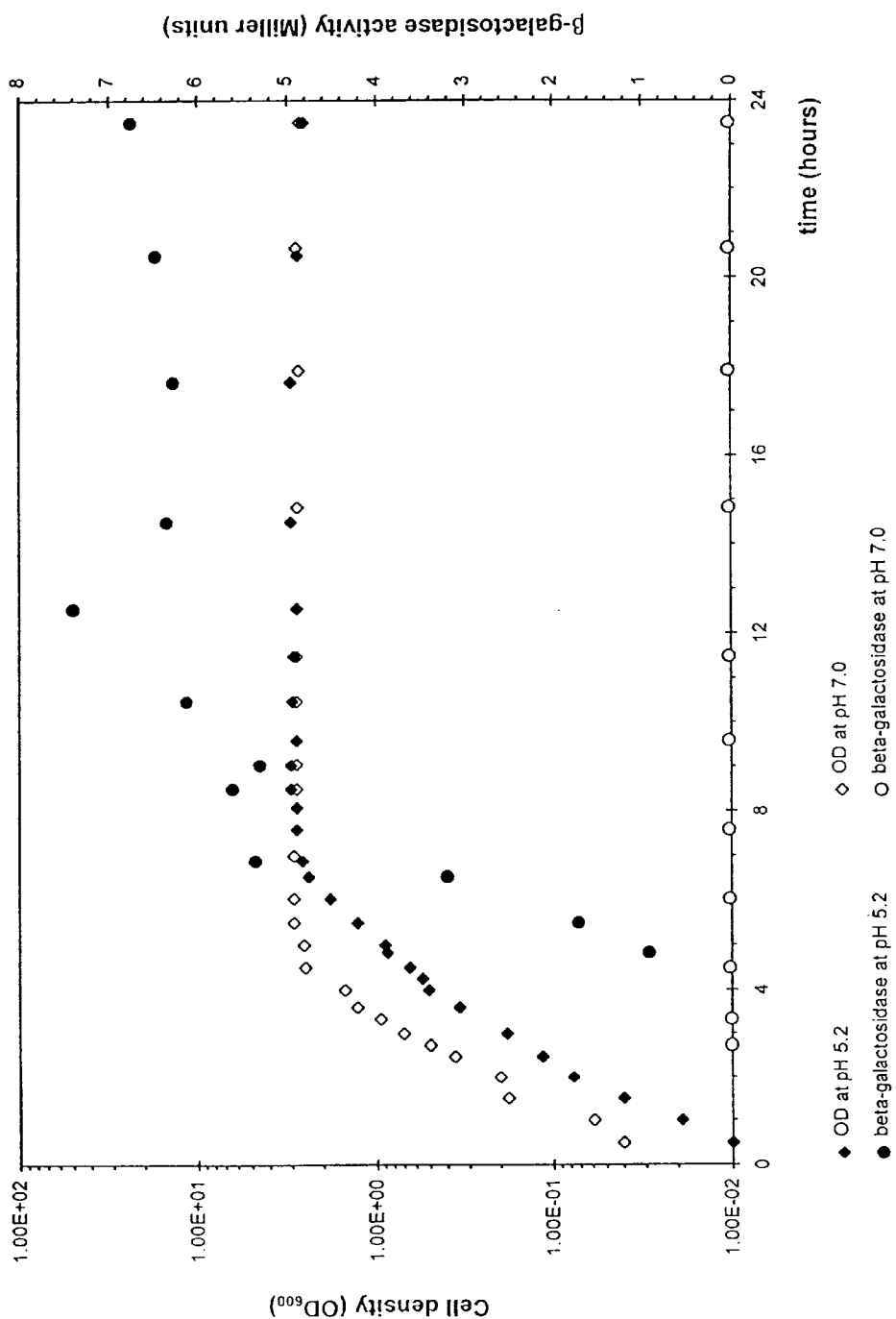
Figure 6:
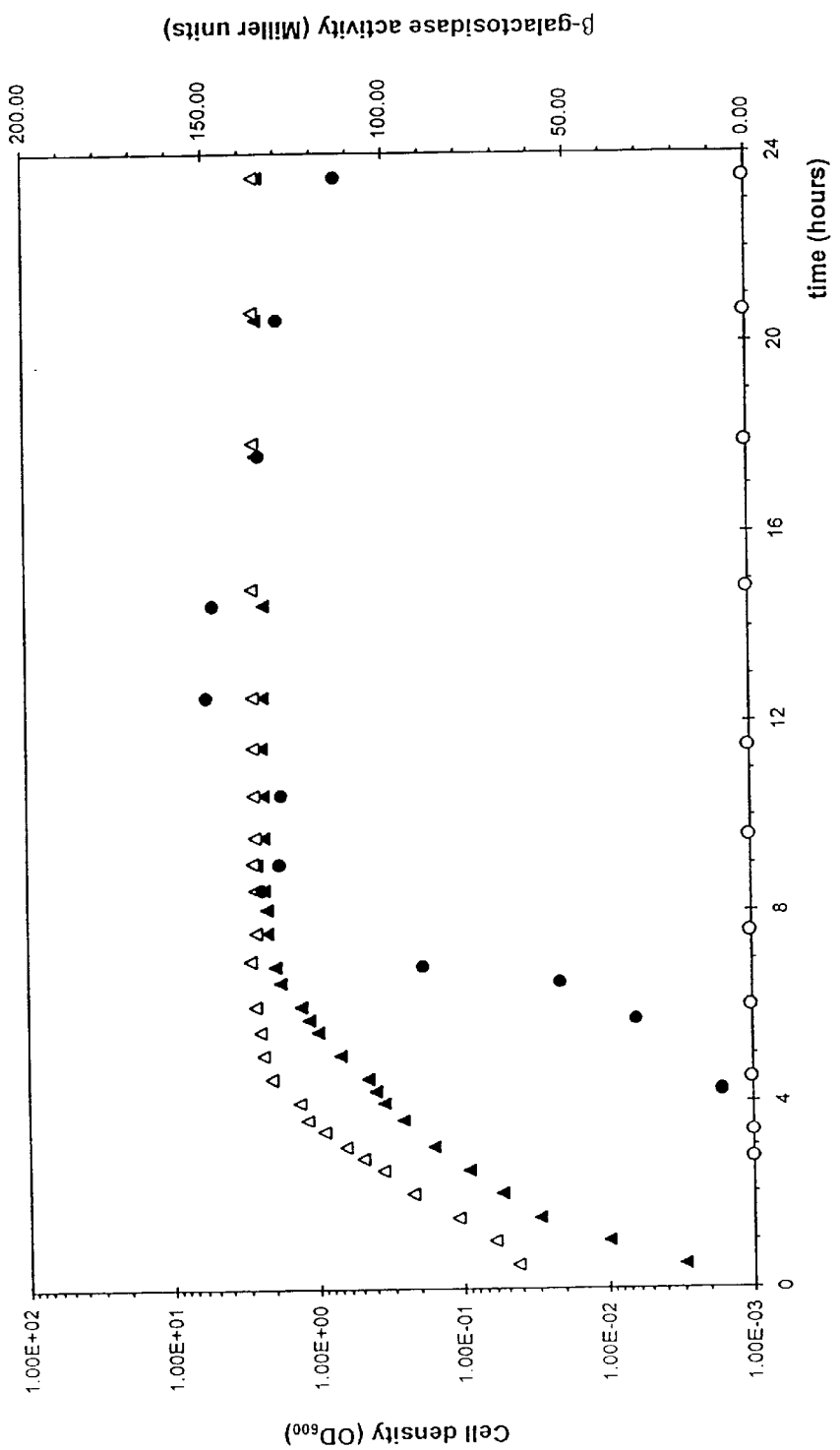
Figure 7:
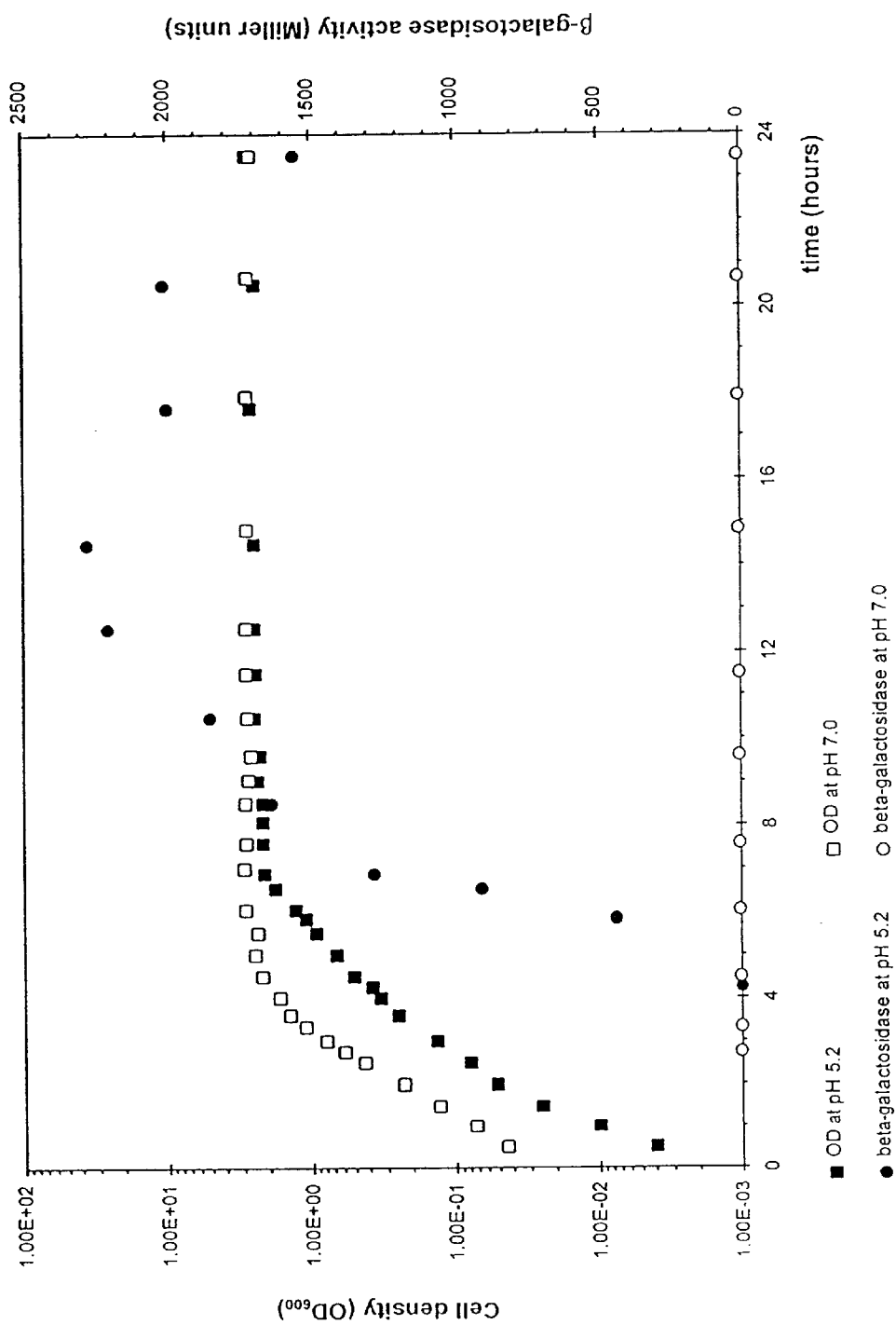
Figure 8:
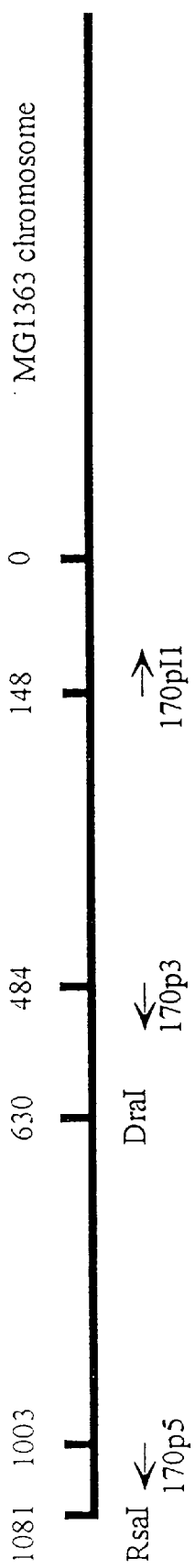
Figure 9:
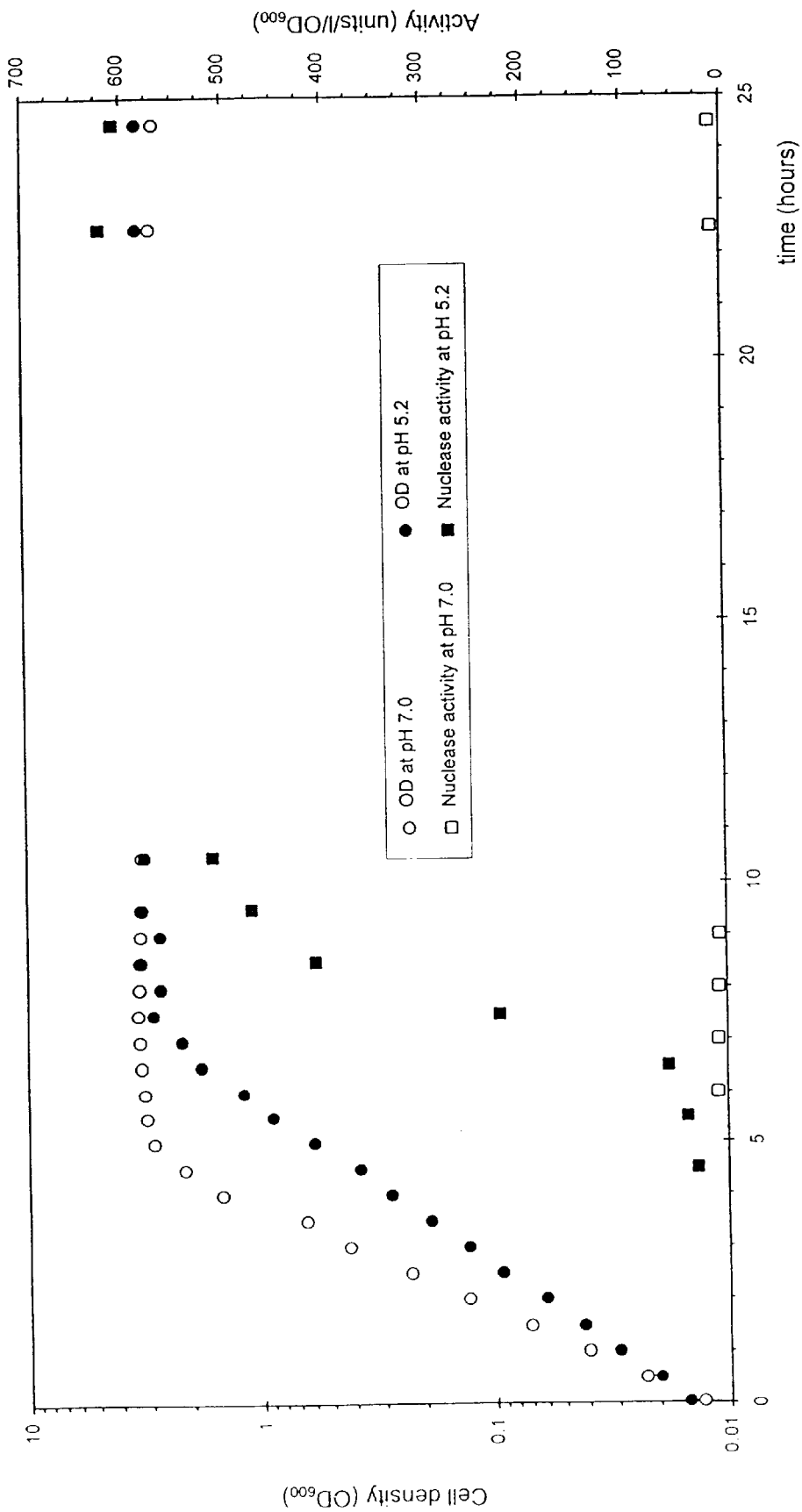
Figure 11:
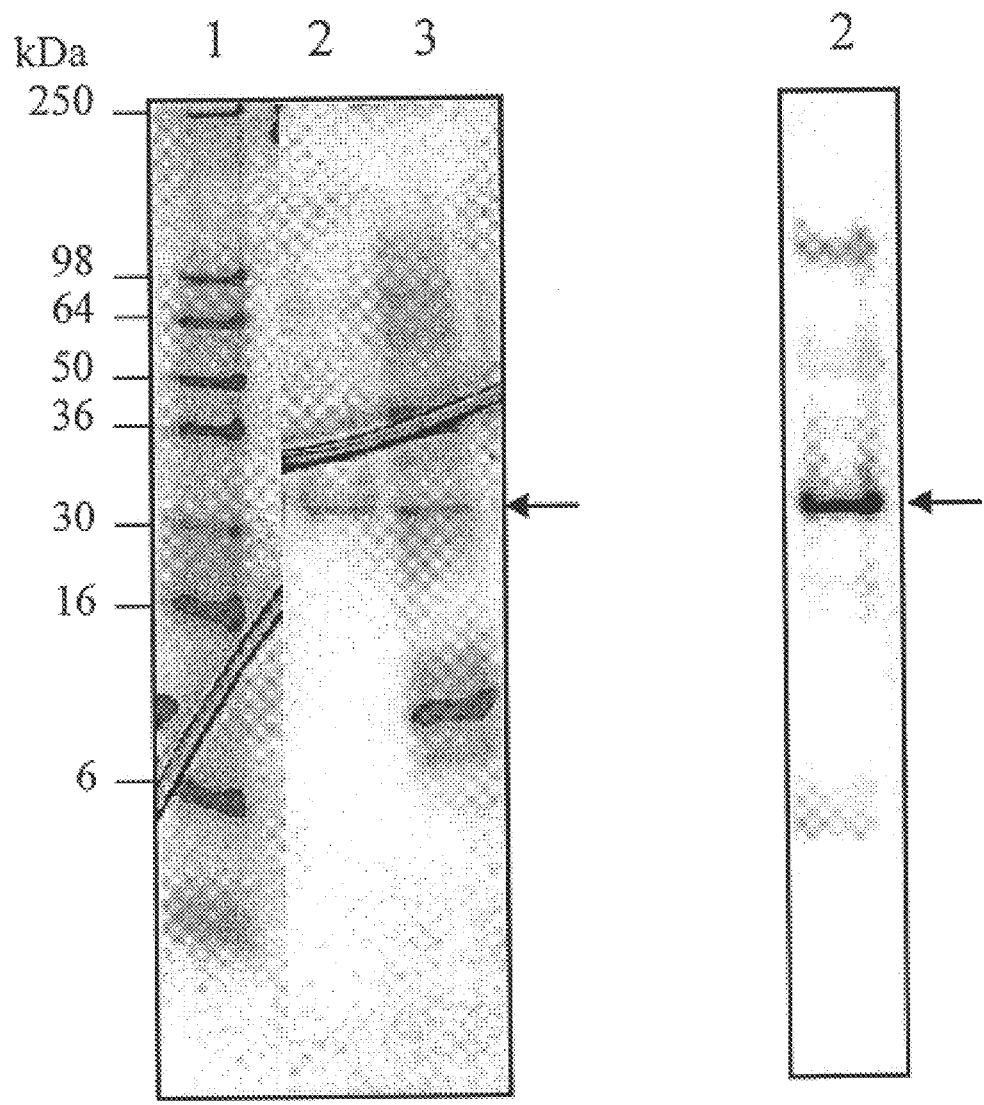
Figure 12:
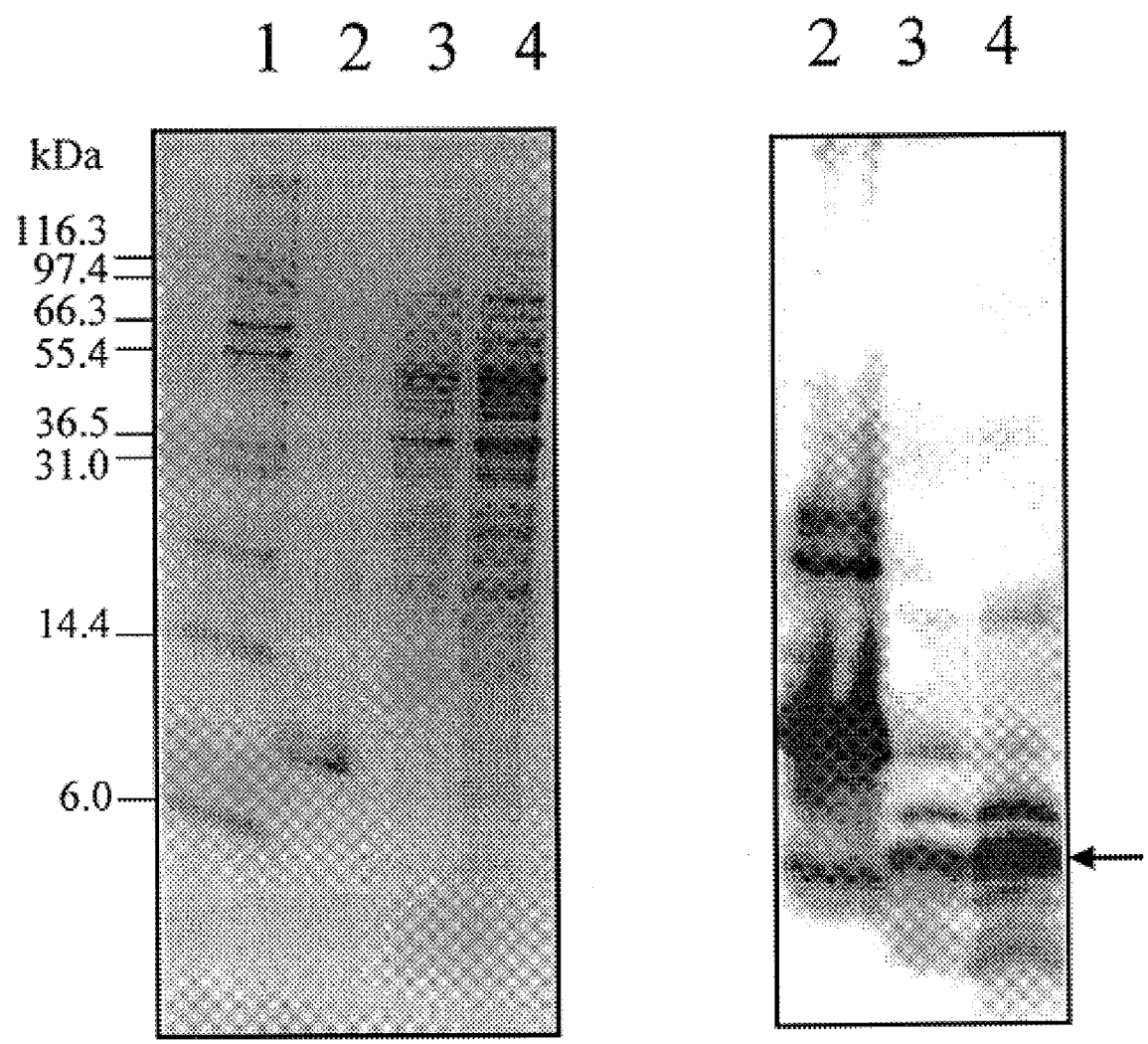
Figure 13:
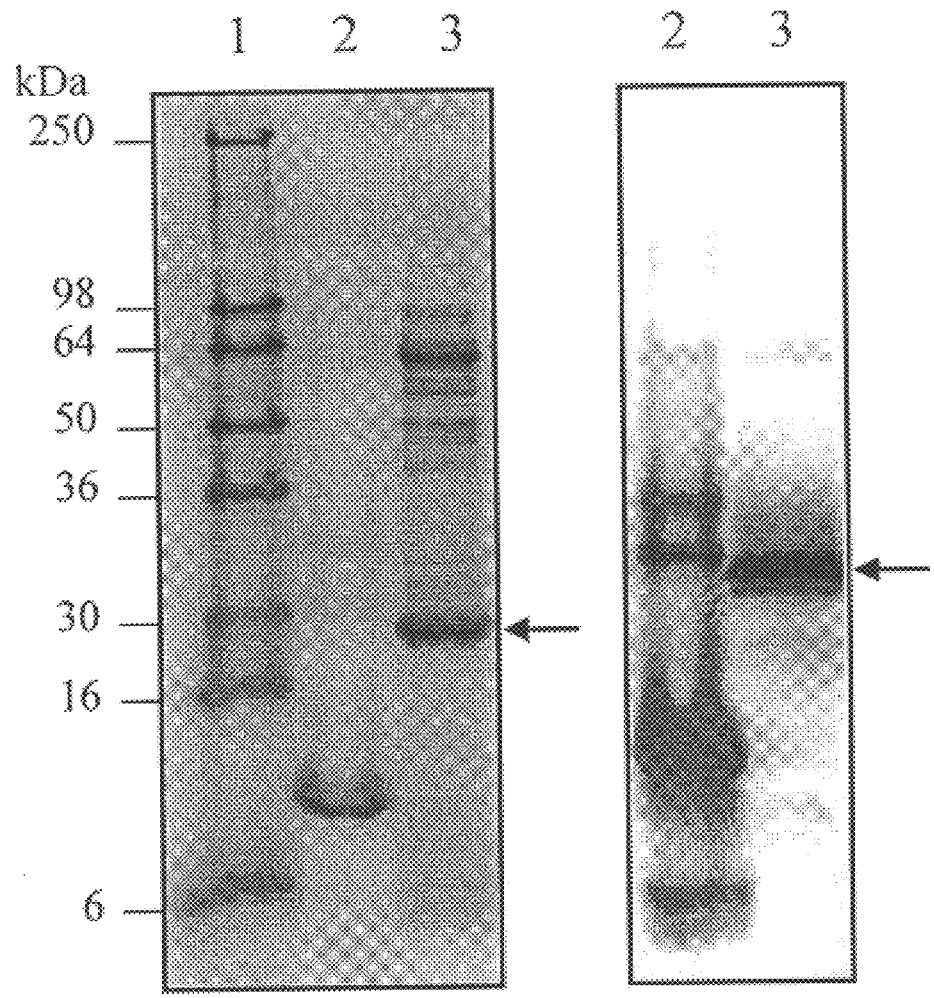

The invention will now be further illustrated in the following examples and the drawing wherein:

FIG. 1 shows a physical map of the chromosomal region located upstream of the Tn917-LTV1 insertion point in integrant strain PA170 (also referred to in WO 94/16086 as P139-170 or 170). The numbers indicate base pair positions relative to the insertion point. The arrows show the orientation and location of PCR primers that were used for construction of strain AMJ547. Only relevant restriction sites are shown. The figure is not drawn to scale;

FIG. 2 is a physical map showing the PCR fragments which have been inserted into the promoter probe vector pAK80. The numbers indicate base pair positions relative to the Tn917 insertion point in the chromosome of the integrant strain PA170. The arrows show the orientation and location of PCR primers that were used for the construction of strains AMJ547, AMJ561, AMJ554, AMJ553, AMJ552 and AMJ551, respectively. The figure is not drawn to scale;

FIG. 3 is a physical map showing the PCR fragments which have been inserted into the promoter probe vector pAK80. The numbers indicate base pair positions relative to the Tn917 insertion point in the chromosome of PA170. The arrows indicate the orientation and location of PCR primers that were used for the construction of strains AMJ553, AMJ569, AMJ568, AMJ567, AMJ566, AMJ565, AMJ577, AMJ558 and AMJ579, respectively. The figure is not drawn to scale;

FIG. 4 is a physical map showing the DNA fragments which have been inserted into pAK80 resulting in the construction of strain AMJ586. The arrows indicate the orientation and location of PCR primers used for the construction. The number indicate base pair positions relative to the Tn917 insertion point in the chromosome of PA170. Only relevant restriction sites are shown. The figure is not drawn to scale;

FIGS. 5, 6 and 7 illustrate β-galactosidase activity and cell density versus time obtained in the fermentation of strains AMJ553, AMJ567, and AMJ586, respectively;

FIG. 8 is a physical map showing the region upstream and downstream, respectively of the Tn917-LTV1 insertion point in integrant PA170. The insertion point is indicated by 0, and numbers indicate base pair positions relative to this point. Restriction sites and primers that were used for the inverse PCR reactions are indicated. The figure is not drawn to scale;

FIG. 9 shows the nuclease activity and cell density versus time obtained during fermentation of strain AMJ627;

FIG. 10A shows the DNA sequence of the 170 bp DNA fragment in plasmid pAMJ553, containing the P170 promoter (SEQ ID NO:26). Base No. 1 is defined as the first base upstream the Tn917 insertion point in integrant PA170, the transcriptional start point is indicated by an asterisk at position 114 above the sequence. The putative extended −10 promoter region is underlined;

FIG. 10B is an enlargement of the wildtype sequence located between bp No. 60 and bp No. 80. The identified mutation(s) in each mutant is (are) shown below the wildtype DNA sequence (SEQ ID NO:27, SEQ ID NO:28, SEQ ID NO:29 AND SEQ ID NO:30, respectively);

FIG. 11 shows SDS-PAGE analysis (left) of proteins secreted by strain AMJ715 (MPT64). Lane 1: molecular weight marker (SeeBlue™, Novex); lane 2: 40 times concentrated supernatant from AMJ715; 3, *M. tuberculosis* H37Rv short-term filtrate. Western blot analysis (right) of proteins secreted by strain AMJ715. Lane 2: 40 times concentrated supernatant from AMJ-715. The arrows show the location of the *M. tuberculosis* antigen MPT64;

FIG. 12 illustrates SDS-PAGE analysis (left) of proteins secreted by strain AMJ700 (ESAT-6). Lanes 1: molecular weight marker (Mark12™, Novex); lane 2: recombinant ESAT-6 preparation from *E. coli;* lane 3: 20 times concentrated supernatant from AMJ700; lane 4: 40 times concentrated supernatant from AMJ700 and western blot analysis (right) of proteins secreted by strain AMJ700. Lanes 2, 3 and 4 are as described for the SDS-PAGE analysis. The arrow shows the location of ESAT-6;

FIG. 13 shows SDS-PAGE analysis (left) of proteins secreted by strain AMJ717 (ESAT-6-ESAT-6). Lane 1: molecular weight marker (SeeBlue™, Novex); lane 2: recombinant ESAT-6 preparation from *E. coli;* lane 3: 40 times concentrated supernatant from strain AMJ717 and western blot analysis (right) of proteins secreted by strain AMJ717 (ESAT-6-ESAT-6). Lanes 2, 3 and 4 are as described for the SDS-PAGE analysis. The arrows show the location of ESAT-6-ESAT-6.

For the understanding of the present invention, reference is made to WO 94/16086 which are hereby incorporated by reference. In the following examples, Examples 4, 6, 8 and 13 from WO 94/16086 have been incorporated as reference Examples 1, 2, 3 and 4, respectively in order to illustrate i.a. the integrant clone P139-170 and the promoter probe vector pAK80. (References in the reference examples to examples, figures or tables are to those in WO 94/16086)

REFERENCE EXAMPLE 1

Production of a collection of Tn917 insertions in *Lactococcus lactis*

In order to prepare a collection of Tn917 insertions in *Lactococcus lactis,* the following procedure was followed:

A single colony of a pTV32-containing *Lactococcus lactis* spp. *lactis* strain MG1614 was inoculated into GM17 medium and grown for 8 to 10 generations with selection for Cm$^r$. One per cent of these cells were grown for 8 to 10 generations in GM17 medium with selection for Em$^r$. The temperature was kept at 30° C. The resulting cells were plated onto GM17 agar plates with selection for Em$^r$. 19 colonies were randomly picked and preparation and digestion of genomic DNA in situ in agarose blocks were done as described in Example 3. FIG. 5 and table 3 show that 12 out of 18 (digestion one clone resulted in fragments which could be visualized as discrete bands) clones had the transposon inserted at the same location on the chromosome indicating that the culture was dominated by a single integrant.

TABLE 3

*L. lactis* spp. *lactis* MG1614 TV32 integrants from a culture containing a dominant integrant

| Group | TV32 target: chromosomal SmaI fragment (kb) | Fragment length (kb) of SmaI-digested target fragments with inserted TV32[a] | Group member (integrant No.) |
|---|---|---|---|
| 1 | 600 | 540 + 70 (= 610) | E15 |
| 2 | 600 | 475 + x | E4 |
| 3 | 600 | 400 + 210 (= 610) | E13, E16 |
| 4 | 310 | 190 + 140 (= 330) | E1, E3, E6, E7, E8, E10, E11, E12, E14, E17, E18, E19 |
| 5 | 200 | x + x | E9[b] |
|   | 140 | x + x |   |
| 6 | 175 | 160 + x | E2 |

[a]indicates a fragment that could not be detected on PFGE gels
[b]Double integrant To circumvent a dominant integrant in a culture, the following procedure was selected:

Strain MG1614 was transformed with pTV32 as described in Example 1. The transformed cells were plated onto SGM17 agar plates containing 1 μg/ml of erythromycin. Following incubation at 30° C. for 48 hours, 20 plates each with about 100 colonies were replica-plated onto plates of GM17 agar with selection for Em$^r$. The replicated plates were incubated at 30° C. for 30 hours. The replication step was repeated and the colonies were washed off and pooled. From the pooled culture, 18 integrants were randomly selected and analyzed by PFGE as defined above. On the basis of the location of the Tn917 insertions on chromosomal SmaI fragments, the 18 integrants were divided into 13 groups of which none contained more than 2 insertions (FIG. 6 and table 4). It was therefore concluded that the pooled culture contained a collection of quasi-randomly transposon TV32-insertions in strain MG1614.

TABLE 4

*Lactococcus lactis* spp. *lactis* MG1614 TV32 integrants from a culture containing quasi-random TV32 insertions

| Group | TV32 target: chromosomal SmaI fragment (kb) | Fragment length (kb) of SmaI-digested target fragments with inserted TV32[a] | Group member (integrant No.) |
|---|---|---|---|
| 1 | 600 | 540 + 70 (= 610) | K10, K20 |
| 2 | 600 | 530 + 80 (= 610) | K3, K12 |

TABLE 4-continued

*Lactococcus lactis* spp. *lactis* MG1614 TV32 integrants from a culture containing quasi-random TV32 insertions

| Group | TV32 target: chromosomal SmaI fragment (kb) | Fragment length (kb) of SmaI-digested target fragments with inserted TV32[a] | Group member (integrant No.) |
|---|---|---|---|
| 3 | 600 | 520 + 90 (= 610) | K9, K18 |
| 4 | 600 | 510 + 100 (= 610) | K13 |
| 5 | 600 | 470 + 120 (= 590) | K14 |
| 6 | 600 | 460 + 140 (= 600) | K17 |
| 7 | 600 | 375 + 220 (= 595) | K4, K6 |
| 8 | 310 | 185 + 140 (= 325) | K2 |
| 9 | 200 | 175 + x | K11 |
| 10 | 140 | 110 + x | K1 |
| 11 | 140 | 105 + x | K5, K16 |
| 12 | 140 | x + x | K7 |
| 13 | 120 | x + x | k8 |

[a]indicates a fragment that could not be detected on PFGE gels

Sterile glycerol was added to the pooled culture at a concentration of up till 25%. and this mixture stored −80° C.

A pooled culture containing a collection of quasi-random LTV1 insertions in *Lactococcus lactis* spp. *lactis* MG1363 was prepared essentially as described above. However, before the washing off and pooling of the colonies the following was carried out:

320 μg/ml of X-gal was added to the plates used for the second replication. 242 colonies with varying blue intensities were seen on the second replication plate. In contrast less than 5% of these colonies were blue on GM17 agar plates containing 40 μg/ml of X-gal incubated for more than 48 hours. (40 μg/ml of X-gal is the standard concentration for identification of lacZ expression in *E. coli*). Each of the 242 blue colonies appearing on the plate containing 320 μg/ml of X-gal were restreaked to obtain single colonies on GM17 containing 1 μg/ml of erythromycin and 320 μg/ml of X-gal followed by restreaking once on the same medium. A single colony from each of these subcultures was inoculated into liquid GM17 medium supplemented with 1 μg/ml of erythromycin and incubated overnight at 30° C. and sterile glycerol added at a concentration of 25% to each of these subcultures for storage at −80° C. These 242 clones are referred to in the following as promoter fusion collection no. 1 (PFC-1).

One of the *Lactococcus lactis* spp. *lactis* MG1363 PFC-1 clones with the designation P139-170 was deposited with the DSM-Deutsche Sammlung von Mikroorganismen und Zellkulturen GmbH, Mascheroder Weg 1b, D-38124 Braunschweig, Germany on 21 December, 1992 under the accession number DSM 7360.

REFERENCE EXAMPLE 2

The construction of a promoter-probe vector for lactic acid bacteria

A useful tool for analysing the conditions that turn on a gene and measuring the level of expression, is a promoter probe. For Lactococcus, pGKV210, a promoter-probe vector based on chloramphenicol acetyl transferase and driven by the pWVO1 replicon has been constructed (van der Vossen et al., 1985). Unfortunately, this vector only provides slightly enhanced chloramphenicol-resistance when promoters are cloned into it (van der Vossen et al., 1987). Translation of mRNA containing the cat-86 gene is activated by chloramphenicol (Alexieva et al., 1988) so that the level of enzyme measured is dependent on two factors, the promoter strength and activation efficiency. In addition, the pWVO1 replicon replicates by rolling-circle replication, and is therefore susceptible to size-dependent segregational instability (Kiewiet et al., 1993).

A promoter-probe vector for Lactococcus and assumingly other lactic acid bacteria was constructed based on the β-galactosidase genes of *Leuconostoc mesenteroides* subsp. *cremoris*, the *Lactococcus lactis* subsp. *lactis* biovar *diacetylactis* citrate plasmid replicon and an erythromycin-resistance marker. This vector is named pAK80. Cloning of the promoter for the tRNA cluster adjacent to the tma gene of CHCC285 showed that this vector functions. The resulting construction, pAK90, produces extremely high levels of β-galactosidase in MG1363.

The β-galactosidase genes from *Leuconostoc mesenteroides* subsp. *cremoris* was cloned and found to be nearly identical to the β-galactosidase gene from *Leuconostoc lactis* (David et al., 1992). Both genes have been shown to be expressed in *Escherichia coli* and in *Lactococcus lactis* strain MG1363. The promoter of the β-galactosidase gene was deleted by polymerase chain reaction (PCR) and replaced with a polylinker, allowing cloning of various DNA fragments and testing for promoter activity. This construction was cloned into a shuttle vector containing the *L. lactis* subsp. *lactis* biovar *diacetylactis* citrate plasmid replicon, the pACYC184 replicon for *E. coli* and a selectable marker (erythromycin-resistance) for both organisms. Cloning of a tRNA promoter into the polylinker gave high levels of β-galactosidase in MG1363, proving that the vector works as planned.

A. Materials and methods

1. Bacterial strains, plasmids and media

MG1363 which is a plasmid-free *Lactococcus lactis* strain (Gasson, 1983). *Escherichia coli* DH5α [supE44 lacΔU169 hsdR17 recA1 endA1 gyrA96 thi-1 relA1 Φ801acZΔM15] (Hanahan, 1983) was used for cloning.

The cloning vectors and relevant markers which were used were: pVA891 [erythromycin resistance; $Em^R$] (Macrina et al., 1983), and pIC19H [ampicillin resistance; $Amp^R$] (Marsh et al., 1984). The various plasmids constructed during the construction of the promoter-probe vector are described in the following.

Lactococcus strains were grown at 30° C. in GM17 medium. *E. coli* strains were grown in LB medium at 37° C. Antibiotics were used at the following concentrations: for *E. coli*; erythromycin, 250 μg/ml; and ampicillin 50 μg/ml; for Lactococcus; erythromycin, 1 μg/ml.

2. Plasmid preparations and transformations

Plasmid DNA for sequencing and electroporations was prepared with the Qiagen plasmid kit (Diagen, Dusseldorf, Germany).

Small scale plasmid preparations from Lactococcus were done essentially according to Israelsen et al. (1993).

Plasmids were introduced into MG1363 by electroporation of glycine-grown competent cells essentially according to Holo and Nes (1989).

3. β-galactosidase assays

Promoter activity was determined by carrying out β-galactosidase assays on overnight cultures grown in G1.5M17 medium. 1 ml of culture was centrifuged at 10,000× g for 10 min. The pellet was resuspended in 500 μl Z buffer (Miller, 1972). 100 μl of cell suspension was mixed with 400 μl of Z buffer, 12.5 μl 0.1% SDS and 25 μl CHCl$_3$ on a Vortex mixer for 10 seconds. After Vortex mixing the suspension was treated as described in Example 7. The results are shown in Table 7.

The assay results are stated as Miller units. One Miller unit=$(1000 \times A_{420})/(time \times volume \times A_{600})$ (where time is in minutes and volume is in ml).

B. Construction of pAK66

Two PCR primers were obtained which allowed amplification of the entire replication region of the citrate plasmid. These had the following sequences:

Primer 1 5'TGAATTCAGAGGTTTGATGACTTTGACC 3' (SEQ ID NO:1)

Primer 4 5'GGAATTCCTAACAAAAGACTATTAACGC 3' (SEQ ID NO:2)

Primer 1 corresponds to nucleotides 610–621 and Primer 4 is complementary to nucleotides 2340–2361 of the citrate plasmid replication region (Jahns et al., 1991). Both contain EcoRI sites at their 5' end to facilitate cloning. The 1.7 kb amplification product was cloned as an EcoRI fragment into pIC19H to produce pKR41. This EcoRI fragment was then moved into the unique EcoRI site of pVA891 to produce the shuttle vector pAK66 which replicates in *E. coli* and *L. lactis* MG1363. The construction of pKR41 has been described in a manuscript submitted for publication (Pedersen et al., 1993).

C. Cloning of the *Leuconostoc mesenteroides* subsp. *cremoris* β-galactosidase gene During the course of cloning and sequencing IS1165 from *Leuconostoc mesenteroides* subsp. *cremoris* strain DB1165 we obtained a clone called pSB1 (Johansen and Kibenich, 1992). This clone contained a 5.8 kb insert in the polylinker of pIC19H. Normally, cloning in pIC19H destroys β-galactosidase activity and colonies with inserts are white on X-gal. pSB1 was strange in that it gave blue colonies on X-gal. DNA sequence analysis revealed that the insert in pSB1 contained the β-galactosidase gene of *Leuconostoc mesenteroides* subsp. *cremoris* and that it was nearly identical to that of *Leuconostoc lactis* (David et al., 1992). Only 3 differences were detected in 830 bp sequenced.

D. Construction of pAK67.7

This construction involved the replacement of the β-galactosidase promoter with a polylinker and insertion of stop codons in all 3 forward reading frames and is illustrated in FIG. 8. The promoter was removed by PCR using two primers:

lac-1   ATAGATCTGCAGGATCCCGGG-TAACTTTGAAAGGATATTCCTC (SEQ ID NO:3)

lac-2 ATTGAGGGTATACGGTGGGCG (SEQ ID NO:4)

The underlined part of lac-1 is identical to the beginning of the β-galactosidase gene and contains the ribosome binding site. The remaining sequence contains a variety of restriction sites including BglII. The lac-2 primer anneals to the β-galactosidase gene, 20 bp downstream of the unique NcoI site. PCR amplification with these primers will amplify from the ribosome binding site to just beyond the NcoI site and produce a 360 bp fragment containing several restriction sites at one end, an NcoI site at the other end and no promoter or other regulatory sequences from the β-galactosidase gene. This 360 bp fragment was purified, digested with BglII and NcoI and cloned into BglII/NcoI digested pSB1. The resulting plasmid was named pAK67 and had the following polylinker preceding the β-galactosidase gene:

```
  H
  i
  n           B    B
  d       X  g    Pa   S
  I       h  l    sm   m
  I       o  I    tH   a
  I       I  I    II   I
AAGCTTTCGCGAGCTCGAGATCTGCAGGATCCCGGGTAACTTTGAAAGGATATTCCTCATG
    (SEQ ID NO:5)
a K   L   S   R   A   R   D   L   Q   D   P   G   *
b  S   F   R   E   L   E   I   C   R   I   P   G   N   F   E   R   I   F   L   M   -
c    A   F   A   S   S   R   S   A   G   S   R   V   T   L   K   G   Y   S   S       - a: (SEQ ID NO:6)
b: (SEQ ID NO:7)
C: (SEQ ID NO:8)
```

DNA sequence analysis revealed that this polylinker was present and that no alterations had been introduced in the β-galactosidase gene by errors during PCR.

As can be seen above, there are two open reading frames that go across the polylinker into the β-galactosidase gene. Since these could potentially interfere with expression of β-galactosidase from promoters inserted into the polylinker, it was decided to introduce stop codons in all three forward reading frames. This was done by obtaining two oligonucleotides with the following sequence:

Stop-1 GGGTCTAGATTA (SEQ ID NO:9)
Stop-2 TAATCTAGACCC (SEQ ID NO:10)

These oligonucleotides are complementary and will anneal to give a 12 bp piece of double stranded DNA containing an XbaI restriction site. This small fragment was cloned into the SmaI site of pAK67. These oligonucleotides were designed in such a way that the SmaI site would be retained, a new XbaI site would be present in plasmids with this tiny insert and stop codons would be introduced into the two open reading frames. The cloning was done by digesting pAK67 with SmaI, phosphatase treating and ligating with a mixture of the two oligonucleotides that had been treated with kinase and allowed to anneal to each other. Transformants were purified and those in which the plasmid had gained an XbaI site were further analyzed. DNA sequence analysis revealed that one clone, pAK67.7 had the desired structure:

This was accomplished by digesting pAK67.7 with HindIII and SalI and ligating into pAK66, also digested with HindIII and SalI. Among the plasmids produced, was pAK80 which was the promoter-probe vector exactly as originally designed.

The plasmid pAK80 harboured by *Lactococcus lactis* spp. *lactis* MG1363 was deposited with the DSM-Deutsche Sammlung von Mikroorganismen und Zellkulturen GmbH, Mascheroder Weg 1b, D-38124 Braunschweig, Germany on Aug. 27, 1993 under the accession number DSM 8496.

F. Testing of pAK80 using two regulatable tRNA promoters

A DNA fragment from *Lactococcus lactis* subsp *lactis* adjacent to the tma gene of CHCC285 has been isolated and found to contain a cluster of tRNA genes preceded by a promoter region (FIGS. 11 and 12) comprising two potential promoters (PI, nucleotides 107–134; PII, nucleotides 215–242). The PI and PII promoters, contained on a 501 bp HindIII-ScaI fragment isolated from the clone pLN39 was cloned by inserting it into pAK80 digested with HindIII and SmaI, in front of the promoterless *Leuconostoc mesenteroides* subsp *cremoris* β-galactosidase gene. Following ligation, MG1363 was electroporated and the cells were plated on regeneration medium (Holo and Nes, 1989) containing erythromycin and X-gal. A total of seven blue colonies were obtained. Plasmid analysis revealed that all seven had identical plasmids and that each contained the desired insertion in pAK80. One plasmid was isolated and

```
  H
  i
  n           B    B
  d       X  g    Pa   S    X
  I       h  l    sm   m    b
  I       o  I    tH   a    a
  I       I  I    II   I    I
AAGCTTTCGCGAGCTCGAGATCTGCAGGATCCCGGGTCTAGATTAGGGTAACTTTGAAAGGATATTCCTCATG
1 ---------+---------+---------+---------+---------+---------+---------+--- 73
TTCGAAAGCGCTCGAGCTCTAGACGTCCTAGGGCCCAGATCTAATCCCATTGAAACTTTCCTATAAGGAGTAC
    (SEQ ID NO:11)
a K   L   S   R   A   R   D   L   Q   D   P   G   S   R   L   G   *
b  S   F   R   E   L   E   I   C   R   I   P   G   L   D   *          β-galactosidase   M -->
c    A   F   A   S   S   R   S   A   G   S   R   V   * a: (SEQ ID NO:12)
b: (SEQ ID NO:13)
C: (SEQ TD NO:14)
```

E. Construction of pAK80

The final step in the production of the promoter-probe vector was the combining of the manipulated β-galactosidase gene with a replicon and selectable marker for Lactococcus.

designated pAK90. β-galactosidase assays revealed that MG-1363/pAK90 produced 5000 Miller units of enzyme, while MG-1363/pAK80 produced 1 Miller units. Thus, the region preceding the tRNA genes contains a very strong promoter.

Searching for sequences with similarity to the sequence of the above promoter region (FIG. 13) revealed a consensus sequence of promoters preceding rRNA operons and tRNA operons from Lactococcus species including a previously undescribed conserved sequence (motif), AGTT. This sequence ends 5 bp upstream of the −35 region and is not conserved in tRNA and rRNA promoters of *Escherichia coli* or *Bacillus subtilis*. In all Lactococcus species where this AGTT motif was found to precede potential rRNA or tRNA promoters, these promoters had all been isolated from plasmids where the promoters were inserted in front of the cat-86 gene coding for chloramphenicol acetyltransferase. Since this enzyme is expressed poorly in *Lactococcus lactis* resistance to chloramphenicol can only be obtained in this organism by cloning strong promoters in front of the cat-86 gene. Therefore it appears that the motif AGTT is found only in strong promoters of *Lactococcus lactis*.

The above promoters PI and PII both contain conserved sequences assumingly involved in stringent control (FIG. 13) and accordingly, these promoters appear to be regulatable promoters.

A 1.0 kb HindIII-EcoRI fragment from pLN39 was inserted into the plasmid pCI3340 digested with HindIII and EcoRI and the resulting plasmid pLN40 was introduced into *Lactococcus lactis* MG1363. pLN40/MG1363 was deposited with the DSM-Deutsche Sammlung von Mikroorganismen und Cellkulturen GmbH, Mascheroder Weg 1b, D-38124 Braunschweig, Germany on Dec. 22, 1993 under the accession numbers DSM 8858.

G. Conclusions

This Example describes the construction of a novel promoter-probe vector for Lactococcus and assumingly other lactic acid bacteria. This vector has several advantages over previously described vectors. It is based on the *Lactococcus lactis* subsp. *lactis* biovar *diacetylactis* citrate plasmid replicon, a theta-replicating plasmid, and so is more stable. The reporter gene chosen is not subject to post-transcriptional control so the enzyme levels can be measured without the presence of any inducers. This is in contrast to plasmids based on the cat-86 gene where chloramphenicol actually activates the translation of the mRNA (Alexieva et al., 988). Enzyme assays and plate assays for the reporter gene are simple and standard procedures in most laboratories.

REFERENCE EXAMPLE 3

Cloning of DNA fragments containing a lactic acid bacterial promoter and assessment of promoter activity in *Lactococcus lactis*

A. Cloning in *E. coli* of EcoRI fragments containing *Lactococcus lactis* DNA and the ColE1 replicon from Tn917-LTV1 integrants Chromosomal EcoRI fragments containing lactococcal DNA, lacZ, cat, bla and the ColE1 replicon, were prepared according to the method described in Example 5 from the Tn917-LTV1 integrants listed in Table 5 below. The fragments were subsequently religated and introduced into *E. coli* DH5α by transformation as described in Maniatis et al. (1982).

The resulting Tn917-LTV1 integrant fragment plasmids were termed p[integrant No], e.g. p86, p143 and pSB. All Tn917-LTV1 integrants from which the fragments were isolated are in *Lactococcus lactis* MG1363 except SB which is Tn917-LTV1 in *Lactococcus lactis* MG1614.

TABLE 5

Regulation parameters for β-galactosidase expression in selected integrants. The parameters are deduced from plate assays

| Integrant No. | Parameter |
|---|---|
| 86 | arg./pH |
| 143 | temp./growth rate |
| 159 | temp./growth rate |
| 162 | arg./pH |
| 163 | arg./pH; pO$_2$ |
| 170 | temp./growth rate; arg./pH |
| 172 | temp./growth rate |
| 179 | arg./pH; NaCl/ion strength |
| 187 | temp./growth rate |
| 188 | temp./growth rate |
| 189 | NaCl/ion strength |
| 192 | temp./growth rate; arg./pH |
| 199 | NaCl/ion strength; arg./pH |
| 201 | temp./growth rate |
| 202 | temp./growth rate |
| 222 | arg./pH |
| 224 | arg./pH |
| 241 | NaCl/ion strength |
| 242 | arg./pH |
| SB | temp./growth rate; arg./pH |

B. Subcloning of Tn917-LTV1 integrant fragment plasmids into the promoter selection vector pGKV210 pGKV210 is a promoter selection vector which contains an erm gene as a selection marker and a promoterless cat-86 gene preceded by a polylinker (van der Vossen et al., 1987). The cat-86 gene is expressed if a DNA fragment carrying a promoter is inserted in the right orientation into the polylinker. The level of chloramphenicol resistance conferred to the host depends on the strength of the promoter.

The integrant fragment plasmids all have a ClaI site located in the DNA originating from the lacZ part of Tn917-LTV1. In order to clone the EcoRI-ClaI fragments from the plasmids, a ClaI site was first introduced into the polylinker of pGKV210 in the following manner: The synthetic DNA linker
5'GATCGCCATCGATGGC 3' (SEQ ID NO:15)
3'CGGTAGCTACCGCTAG 5' (SEQ ID NO:16)

containing a ClaI site was cloned into the unique BamHI site of pGKV210 as described by Maniatis et al. (1982). The obtained plasmid was termed pGKV210(ClaI). 50 ng of pGKV210(ClaI) digested with ClaI and EcoRI was mixed and ligated with 200 ng of purified ClaI-EcoRI fragment as defined above. This was done with ClaI-EcoRI fragments from the following integrant fragment plasmids: p143, p162, p163, p170, p172, p224, p237, p242 and pSB.

p162 contains an additional ClaI site located in the lactococcal DNA. The fragment from the EcoRI site of this plasmid to the additional ClaI site was inserted into pGKV210(ClaI) All of the DNA recombination work in this Example was carried out according to Maniatis et al. (1982).

The resulting pGKV210 derivative constructs were termed pGKV210:[integrant No], e.g. pGKV210:143, pGKV210:162 and pGKV210:SB. The pGKV210 derivatives were introduced into *E. coli* MC1000 (F-, araD139 (Δara-leu)7679, galU, galK(Δlac)X74, rpsL(Strr), thi) according to the method as described in Example 5. The pGKV210 derivatives were extracted as described in Maniatis et al. (1982) from the transformed host strain. For each extracted pGKV derivative, 1 μg of DNA was introduced into *Lactococcus lactis* MG1363 according to the method as described in Example 1. The resulting transformants (pGKV/MG1363 derivatives) were designated pGKV210:[integrant No]/MG1363, e.g. pGKV210:143/MG1363.

The promoter activity of the above cloned fragments and of previously published pGKV210 derivatives in *Lactococcus lactis* IL1403 (van der Vossen et al., 1987) were determined by plating overnight culture of the pGKV/MG1363 derivatives onto GM17 plates supplemented with 5 mg/l erythromycin and increasing concentrations of chloramphenicol. The concentrations of chloramphenicol were 4, 6, 8, 12, 16, and 20 mg/l, respectively. 50 µl of a $10^4$ times diluted culture in a 0.9% NaCl aqueous suspension were plated on plates with 4–8 mg/l of chloramphenicol. 100 µl of a $10^4$ times diluted culture in 0.9% NaCl were plated on plates containing 12–20 mg/l of chloramphenicol. The plates were incubated at 30° C. for about 80 hrs and the maximum concentration of chloramphenicol still allowing growth was determined. Results are shown in Table 6 below.

Only two pGKV/MG1363 derivatives were resistant to more than 4 mg/l chloramphenicol. However, difficulties in the interpretation of the results were encountered e.g. due to the appearance of small colonies and this assay seems to be inadequate for promoters of medium or weak strength. The pGKV244/IL1403 and pGKV259/IL1403 produce 0,2 and 5.1 units, respectively, when assayed for chloramphenicol acetyltransferase activity (van der Vossen et al., 1987).

TABLE 6

Maximum chloramphenicol (Cm) levels allowing growth of strain MG1363 harbouring pGKV210 and pGKV210 derivatives

| Plasmid harboured by MG1363 | Concentration of Cm (g/ml) |
| --- | --- |
| pGKV210 | <4 |
| pGKV244 | 8 |
| pGKV259 | 16 |
| pGKV210:143 | 4 |
| pGKV210:162 | 4 |
| pGKV210:163 | <4 |
| pGKV210:170 | <4 |
| pGKV210:172 | 8 |
| pGKV210:224 | <4 |
| pGKV210:237 | 4 |
| pGKV210:242 | <4 |
| pGKV210:SB | 12 |

C. Subcloning of Tn917-LTV1 integrant fragment plasmids into the promoter selection vector pAK80 pAK80 is a promoter selection vector which contains an erm gene as a selection marker and a promoterless β-galactosidase gene preceded by a polylinker. The construction of pAK80 is described in Example 6.

The following DNA operations and transformations were carried out according to Maniatis et al. (1982). The integrant fragment plasmids as described above were first subcloned into the cloning vector pGEM-7Zf(+) (Promega) due to the lack of appropriate restriction sites in pAK80. 50 ng of pGEM-7Zf(+) digested with ClaI and EcoRI was mixed under ligation conditions with 200 ng of purified ClaI-EcoRI fragments containing lactococcal DNA from an integrant fragment plasmid. This was done with ClaI-EcoRI fragments from the following plasmids: p143, p162, p163, p224, p242 and pSB, respectively.

p170 contains a SalI site located in the lactococcal DNA. The fragment from the ClaI site to this SalI site was inserted into the cloning vector pBluescript II KS (Strategene) which was digested with ClaI and SalI. This construct was termed pBluescript:170. Extracted plasmid DNA from this construction was digested with XhoI and ClaI and ligated to pGEM-7Zf(+) digested with XhoI and ClaI. The pGEM-7Zf(+) constructions were termed pGEM:[integrant No], e.g. pGEM:143 and pGEM:170 and collectively designated pGEM derivatives. The pGEM derivatives were introduced into *E. coli* strain DH5α as described in Example 5. The DH5α transformants were termed pGEM/DH5α derivatives.

Plasmid DNA from the pGEM/DH5α derivatives were extracted, digested with XhoI and BamHI and ligated to pAK80 digested with XhoI and BamHI. The resulting constructions were termed pAK80:[integrant No], e.g. pAK80:143 and pAK80:170 and collectively designated pAK80 derivatives. The pAK80 derivatives were introduced into *E.coli* MC1000 as described in Example 5. The MC1000 transformants were designated pAK80/MC1000 derivatives. The pAK80 derivatives were extracted from the pAK80/MC1000 derivatives. For each extracted pAK80 derivative 1 µg DNA was introduced into *Lactococcus lactis* MG1363 as described in Example 5. The resulting transformants were termed pAK80:[integrant No]/MG1363, e.g. pAK80:143/MG1363 and pAK80:170/MG1363 and collectively designated pAK80/MG1363 derivatives.

The promoter activity of the cloned fragments were determined by carrying out β-galactosidase assays on overnight cultures of the pAK80/MG1363 derivatives grown in G1.5M17 medium. 1 ml of culture was centrifuged at 10,000× g for 10 min. The pellet was resuspended in 500 µl Z buffer (Miller, 1972). 100 µl of cell suspension was mixed with 400 µl of Z buffer, 12.5 µl 0.1% SDS and 25 µl $CHCl_3$ on a Vortex mixer for 10 seconds.

After Vortex mixing the suspension was treated as described in Example 7. The results are shown in Table 7.

TABLE 7

β-galactosidase activity of strain MG1363 harbouring pAK80 and PAK80 derivatives

| Plasmid harboured by MG1363 | β-galactosidase activity (Miller units) |
| --- | --- |
| pAK80 | 1 |
| pAK80:SB | 820 |
| pAK80:143 | 240 |
| pAK80:162 | 80 |
| pAK80:163 | 1 |
| pAK80:170 | 30 |
| pAK80:224 | 1 |
| pAK80:242 | 1 |

It is clearly demonstrated from the above results that the promoter selection vector pAK80 is capable of discriminating even weak promoters, since pAK80:163/MG1363, pAK80:170/MG1363, pAK80:224/MG1363 and pAK80:242/MG1363 appear to be without promoter activity when assayed for chloramphenicol resistance, but when assayed for β-galactosidase activity it is evident that pAK80:170/MG1363 in contrast to the three other pAK80/MG1363 derivatives, has promoter activity.

The following pAK80/MG1363 derivatives: pAK80:SB/MG1363, pAK80:143/MG1363, pAK80:162/MG1363, pAK80:163/MG1363, pAK80:170/MG1363, respectively were deposited with the DSM-Deutsche Sammlung von Mikroorganismen und Cellkulturen GmbH, Mascheroder Weg 1b, D-38124 Braunschweig, Germany on Aug. 27, 1993 under the accession numbers DSM 8495, DSM 8497, DSM 8498, DSM 8499 and DSM 8500, respectively.

The ClaI-EcoRI fragments from p172 and p215, respectively, containing the lactococcal DNA, were cloned into pGEM-7Zf(+). The pGEM-7Zf(+) constructions were termed as described above in this Example.

The pGEM-7Zf(+) constructions were digested with BamHI and XhoI and ligated to pAK80, also digested with BamHI and XhoI. The details of the cloning experiments were as described above. pGEM:172 was digested with XhoI and BamHI. The ligation mixture was introduced into *E. coli* DH5α, and the resulting plasmid, pAK80:172, was introduced into *Lactococcus lactis* MG1363. pAK80:172/MG1363 is blue on GM17 containing X-gal which demonstrates the presence of a promoter on the 4.5 kb ClaI-EcoRI fragment of p172.

The lactococcal DNA segment of pGEM:215 contains an internal BamHI site. The distal BamHI-XhoI fragment of pGEM:215 was ligated to pAK80 digested with BamHI and XhoI and the lactococcal BamHI-BamHI fragment was ligated to pAK80 digested with BamHI. Each ligation mixture was introduced into *E. coli* DH5α. The resulting plasmids were designated pAK80:215A and pAK80:215B, respectively. The correct orientation of the BamHI fragment in pAK80:215B was verified by restriction map analysis. A subsequent introduction of pAK80:215A and pAK80:215B, respectively, into *Lactococcus lactis* revealed that none of the plasmids harboured a promoter. This result suggests that a potential promoter on ClaI-EcoRI fragments from p215 had been inactivated during cloning of the two subfragments or that the promoter responsible for β-galactosidase expression in Integrant 215 is located upstream of the EcoRI site.

Measurements on overnight cultures of *Lactococcus lactis* MG1363 containing the plasmids pAK80:SB, pAK80:143, pAK80:162, pAK80:170 and pAK80:172, respectively, are described in Example 13 below. However, in Example 13 these plasmids are designated pSMA332, pSMA337, pSMA338, pSMA339 and pSMA345, respectively.

REFERENCE EXAMPLE 4

Mapping of the promoter, P170 on the 9.7 kb EcoRI-ClaI DNA fragment from p170

The following experiments were carried out to map the location of the pH/growth phase regulated promoter, P170 on the 9.7 kb ClaI-EcoRI fragment of p170.

The 9.7 kb ClaI-EcoRI fragment of p170 was cleaved into subfragments and a restriction map was created (see FIG. 16). Appropriate subfragments were subsequently cloned into the promoter probe vector PAK80. However, it was necessary first to create compatible restriction sites on the subfragments and pAK80.

(i) Construction of pSMA344

Cloning of the large 9.7 kb ClaI-EcoRI fragment from p170 into pGEM-7Zf(+) was done by digesting p170 with ClaI and EcoRI followed by ligation of the 9.7 kb fragment to pGEM-7Zf(+) digested with ClaI and EcoRI. The ligation mixture was introduced into *E.coli* DH5α and the resulting plasmid was termed pSMA212. pSMA212 was digested with XhoI and BamHI and ligated to pAK80 also digested with XhoI and BamHI. The ligation mixture was introduced into *E.coli* DH5α.

The resulting plasmid, pSMA344, was subsequently introduced into *Lactococcus lactis* MG1363.

(ii) Construction and cloning of deletion derivatives of the 9.7 kb ClaI-EcoRI fragment from p170

Plasmid pSMA342 was constructed in the following manner:

pSMA212 was digested with ClaI and NdeI, the sticky ends were filled in by use of Klenow polymerase as described by Maniatis et al. (1982). The large 8.7 kb fragment [3 kb from pGEM-7Zf(+) and 5.7 kb from the Lactococcus chromosome] was purified, religated, and introduced into *E.coli* DH5α. The resulting plasmid, pSMA213, was digested with XhoI and BamHI and the purified 5.7 kb fragment was ligated to pAK80 also digested with XhoI and BamHI. The ligation mixture was introduced into *E.coli* DH5α and the resulting plasmid, pSMA342, was subsequently introduced into *Lactococcus lactis* MG1363.

The plasmid pSMA343 was constructed in the following manner: pSMA212 was digested with ClaI and SalI, the sticky ends were filled in by Klenow polymerase. The 6.2 kb fragment [3 kb from pGEM-7Zf(+) and 3.2 kb from the Lactococcus chromosome] was purified, religated and introduced into *E.coli* DH5α. The resulting plasmid, pSMA214, was digested with XhoI and BamHI and the 3.2 kb lactococcal fragment was ligated to pAK80 digested with XhoI and BamHI. The resulting plasmid, pSMA343, was introduced into *E.coli* DH5α and subsequently into *Lactococcus lactis* MG1363.

The plasmid pAK80:170 (DSM 8500) as described in Example 8 is in the following designated pSMA339.

Plasmid pSMA340 was constructed in the following manner: The cloning of the 6.5 kb ClaI-SalI lactococcal fragment from p170 into the cloning vector pBluescript II KS is described in Example 8. This construct being termed pBluescript:170 in Example 8 is designated pSMA201 in the following. pSMA201 was digested with NdeI and SalI and treated with Klenow polymerase to fill in the sticky ends. The large 7 kb fragment [3 kb from pGEM-7Zf(+) and 4 kb from the lactococcus chromosome] was purified, religated and introduced into *E.coli* DH5α. The resulting plasmid was termed pSMA202.

pSMA202 was digested with XhoI and BamHI, and the 4 kb lactococcal fragment was purified and ligated to pAK80, also digested with XhoI and BamHI. The ligation mixture was introduced into *E.coli* DH5α and the resulting plasmid, pSMA340, was subsequently introduced into *Lactococcus lactis* MG1363. pSMA341 was constructed in the following manner:

pSMA202 was digested with NdeI and EcoRI and treated with Klenow polymerase to fill in the sticky ends. The large 5.5 kb fragment [3 kb from pGEM-7Zf(+) and 2.5 kb from the lactococcus chromosome] was purified, religated and introduced into *E.coli* DH5α. The resulting plasmid, pSMA208 was digested with XhoI and BamHI and the 2.5 kb lactococcal fragment was ligated to pAK80, also digested with XhoI and BamHI. The resulting plasmid, pSMA341, was introduced into *E.coli* DH5α and subsequently into *Lactococcus lactis* MG1363.

(iii) Assessment in *Lactococcus lactis* of promoter activity on the subfragments of the 9.7 kb fragment from p170

A plate assay for determination of promoter activity of the cloned lactococcal fragments was performed by plating overnight cultures of *Lactococcus lactis* containing the plasmids pSMA339, pSMA340, pSMA341, pSMA342, pSMA343 and pSMA344, respectively, on GM17 supplemented with 1 μg/ml Em and 160 μg/ml X-gal. Surprisingly, all cultures appeared blue on these plates, showing the existence of at least one functional promoter on all plasmids. From these results it is evident that at least three promoters are located within the lactococcal 9.7 kb fragment from p170.

The *Lactococcus lactis* MG1363 strains containing pSMA339, pSMA340, pSMA341, pSMA342, pSMA343 and pSMA344, respectively, were streaked on GM17 plates and on ArgM17 plates, respectvely. Both type of plates contained 1 μg/ml Em and 160 μg/ml X-gal. The platings were done to identify the pH regulated promoter(s) among the three promoters. Based on these assays the β-galactosidase expression arising from pSMA339, pSMA340 and pSMA344, respectively, was found to be regulated by pH/arginine. The β-galactosidase expression arising from pSMA342 was weakly regulated by pH/arginine, whereas the expression from pSMA341 and pSMA343 were unaffected by these factors.

The results demonstrate that the promoter located on the 4 kb ClaI-NdeI fragment proximal to the f-galactosidase reporter gene, is pH regulated. This promoter is in the following referred to as P170. The plasmid pSMA342, which contains the 5.7 kb lactococcal fragment extending from the NdeI site to the EcoRI site, most likely contains two promoters, of which the one located proximally to the reporter gene also appears to be pH regulated. However, this regulation seems to be dependent on the 3.2 kb EcoRI-SalI fragment located upstream. This conclusion is based on the observation that the promoter harboured on pSMA341 which lacks the 3.2 kb EcoRI-SalI fragment, is not regulated by pH/arginine.

Measurements of β-galactosidase expression in overnight cultures of strain MG1363 containing pSMA339, pSMA340, pSMA341, pSMA342, pSMA343, and pSMA344, respectively, were performed as described in Example 7. All cultures were grown in GM17 medium and ArgM17 medium, respectively. Both media were supplemented with 1 μg/ml Em. As a control of regulated β-galactosidase expression, Integrant 170 was included in the experiment. The results are shown in Table 13:

TABLE 13

β-galactosidase expression in deletion derivatives of the 9.7 kb ClaI-EcoRI fragment of p170

|  | Miller units in GM17 (final pH 5.6–5.8) | Miller units in ArgM17 (final pH 6.6–6.8) | Miller Units in GM17 vs ArgM17 |
|---|---|---|---|
| Integrant 170 | 1.7 | 0.1 | 17 |
| L. lactis MG1363 containing plasmid | | | |
| pSMA339 | 15 | 1 | 15 |
| pSMA340 | 16 | 1 | 16 |
| pSMA341 | 7 | 7 | 1.0 |
| pSMA342 | 2.1 | 1.5 | 1.4 |
| pSMA343 | 22 | 8 | 2.8 |
| pSMA344 | 14 | 1 | 14 |

Lactococcus lactis containing pSMA339, pSMA340 or pSMA344, show the same regulated expression of β-galactosidase as Integrant 170. This shows that the promoter P170 is regulated also when located on the a multicopy plasmid like pAK80. In contrast, the promoter carried on pSMA342 does not show a regulated expression. The promoter harboured on pSMA343 is regulated by pH or arginine. This regulation was not detected in the plate assay. This might be due to differences in the growth on plates and in liquid medium. The regulation observed on the promoter harboured on pSMA343 is not as tight as the regulation of P170.

Fine mapping of the promoter P170 located on the 4 kb ClaI-NdeI fragment of p170

Prior to fine mapping of P170 located on the 4 kb ClaI-NdeI fragment of p170, a more detailed restriction map of the 4 kb ClaI-NdeI fragment was produced (FIG. 17).

The 4 kb ClaI-NdeI lactococcal fragment of p170 is harboured on pSMA202. pSMA202 contains three HindIII sites, of which two are located within the lactococcal DNA and one in the polylinker region. Insertion into pAK80 of the 1.3 kb HindIII fragment, extending from the HindIII site in the polylinker to the HindIII site in the Lactococcus DNA resulted in the plasmid, pSMA357. The insert in pSMA357 contained no promoter activity when introduced into Lactococcus lactis MG1363.

The 2.3 kb. HindIII fragment on the 4 kb ClaI-NdeI fragment was cloned into pAK80 digested with HindIII. The resulting plasmid, pSMA348, was introduced into Lactococcus lactis MG1363. From this plasmid β-galactosidase was expressed, which demonstrates the existence of a functional promoter within this HindIII fragment. A 1.5 kb HincII fragment was inserted into the SmaI site of pAK80 and the resulting plasmid, pSMA358, was introduced into Lactococcus lactis MG1363. β-galactosidase was expressed from pSMA358. The 1.5 kb HincII fragment covers most of the 1.3 kb HindIII fragment and has a 400 bp overlap with the adjacent 2.3 kb HindIII fragment. Based on promoter activity assessments on the inserts in the plasmids pSMA348, pSMA357 and pSMA358, the promoter P170 was mapped to a 400 bp HincII-HindIII fragment located about 1.3 kb upstream of Tn917-LTV1 insertion in Integrant 170.

(iv) Mapping of the promoter PSB

From the sequencing of the upstream located DNA of SB a consensus promoter was identified [see Example 12 (i)] within a 190 bp HpaI-ClaI fragment. pSB was digested with HpaI and ClaI and the fragment was ligated to pNZ336 (Simons et al., 1990) digested with HpaI and ClaI. The resulting plasmid, pNZ336:SB, was digested with SalI and BamHI. The 190 bp fragment was ligated to pAK80, digested with XhoI and BamHI.

The ligation mixture was introduced into E. coli DH5α, and the resulting plasmid, pSMA347 was subsequently introduced into Lactococcus lactis MG1363. Strain MG1363/pSMA347 expresses β-galactosidase, which demonstrate the existence of a functional promoter on the 190 bp fragment.

(v) Measurements on induced and non-induced overnight cultures of Lactococcus lactis MG1363 containing promoter harbouring pAK80 derivatives In Table 14, β-galactosidase activities on overnight cultures grown under induced and non-induced conditions, respectively, are given. The different growth conditions are temperature variations and variation of pH/concentration of arginine in the growth medium, respectively. The strains analyzed include both pAK80 derivatives containing EcoRI-ClaI fragments from the rescue plasmids and, based on the above mapping analyses, pAK80 derivatives containing deletions of the EcoRI-ClaI fragments. The growth of cultures as well as the β-galactosidase assay were performed as described in Example 11. In this example 5Arg1.5M17 is designated as 5ArgM17.

TABLE 14a

β-Galactosidase activities in overnight cultures grown at induced and non-induced conditions. Expression controlled by arginine and/or medium pH (30° C.)

|  | MEDIUM | | |
|---|---|---|---|
| L. lactis containing plasmid | GM17 (final pH 5.6–5.8) | ArgM17 (final pH 6.6–6.8) | 5ArgM17 (final pH 7.7–7.8) |
| pSMA332 | 680 | 560 | |
| pSMA347 | 720 | 620 | |
| Integrant SB: | 6 | 18 | |
| pSMA338 | 70 | 100 | 260 |
| Integrant 162 | 18 | 51 | 140 |

TABLE 14a-continued

β-Galactosidase activities in overnight cultures grown at induced and non-induced conditions. Expression controlled by arginine and/or medium pH (30° C.)

| | MEDIUM | | |
|---|---|---|---|
| L. lactis containing plasmid | GM17 (final pH 5.6–5.8) | ArgM17 (final pH 6.6–6.8) | 5ArgM17 (final pH 7.7–7.8) |
| pSMA339 | 15 | 1 | 0.4 |
| pSMA340 | 16 | 1 | 0.7 |
| pSMA344 | 14 | 1 | 0.5 |
| Integrant 170 | 1.7 | 0.05 | 0.08 |

TABLE 14b

β-Galactosidase activities in overnight cultures grown at induced and non-induced conditions. Expression controlled by temperature (G1.5M17 medium)

| PLASMID | 30° C., 20 hrs | 15° C., 165 hrs |
|---|---|---|
| pSMA337 | 190 | 35 |
| Integrant 143 | 0.8 | 1.5 |
| pSMA339 | 27 | 67 |
| pSMA344 | 21 | 75 |
| Integrant 170 | 1.7 | 14 |
| pSMA347 | 650 | 120 |
| Integrant SB | 6 | 18 |
| pSMA345 | 36 | 1.4 |
| Integrant 172 | 1.4 | 0.9 |

The results show that the promoter from pSB is not pH regulated when harboured on pAK80. This result is seen with both pSMA332 and pSMA347. The temperature regulation of the promoter from pSB is reversed when located on pAK80. The promoter from p162 is still regulated when located on pAK80. However, the total expression of β-galactosidase from the plasmid harboured promoter is not as high as expected from the high copy number of pAK80. The pH regulation of P170 is described above. The temperature regulation of P170 is conserved, although to a lesser extent, when located on pAK80. The promoter from p143 is regulated when located on pAK80. However, this regulation is opposite to the regulation observed when the promoter is chromosomally located. The strength of the promoter on p143 is increased dramatically when plasmid located. β-galactosidase expression from the promoter on p172 is slightly influenced by temperature when located on the chromosome. This regulation becomes much more pronounced when the promoter is plasmid located.

The results clearly demonstrate that regulation of a chromosomal promoter is in general dependent on the location, i.e. whether it is chromosomally or multicopy extrachromosomally located. It is contemplated that had a conventional promoter cloning strategy including shotgun cloning in a promoter cloning vector been used, the results concerning regulation would in most cases have been quite different from those obtained using the above strategy which included studies on regulation directly on chromosomally located promoters.

EXAMPLE 1
Minimizing a DNA fragment containing the P170 promoter

The pH regulated promoter P170 from *Lactococcus lactis* MG1363 is located on a 9.7 kp DNA fragment (Israelsen et al., 1995), which also includes a small fragment of Tn917 DNA originating from the rescue of P170 from the *L. lactis* MG1363 chromosome. The Tn917 DNA fragment was found to interfere with the transcription directed by P170 and was subsequently eliminated by subcloning of P170.

A DNA fragment comprising P170 was PCR amplified from the *L. lactis* MG1363 chromosome using the primers designated 170 BamHI and 170p3R, which are complementary, respectively, to the DNA sequence located immediately upstream the Tn917 insertion point, and a sequence located 623 bp further upstream of this point (FIG. 1). This amplified DNA fragment contains an EcoRV site located 205 bp upstream of the Tn917 insertion point and a BamHI site located in the 5' end of primer 170 BamHI. The PCR fragment was digested with EcoRV and BamHI, and a 205 bp fragment was inserted into pKS Blue-script II digested with EcoRV and BamHI, generating pSMA470. pSMA470 was subsequently digested with XhoI (multiple cloning site) and BamHI, and the 205 bp fragment comprising P170 DNA sequence was cloned into the promoter cloning vector pAK80, generating plasmid pAMJ547. The β-galactosidase activity expressed from this strain was subsequently determined (Miller, 1972) in samples obtained from corresponding sets of cultures grown overnight in either GM17 medium or ArgM17 medium.

The enzyme activities (Table 1.1) show that both promoter activity and pH regulation are contained on the 205 bp DNA fragment originating from integrant PA170.

TABLE 1.1

β-Galactosidase activities (Miller Units) in strains of *L. lactis* grown overnight in GM17 (pH about 5.5 after growth) or ArgM17 (pH about 7.0 after growth)

| | β-Galactosidase activity | |
|---|---|---|
| *Lactococcus lactis* strain | GM17 | ArgM17 |
| AMJ547 | 4.3 | 0.9 |
| AMJ561 | 3.5 | 0.2 |
| AMJ554 | 3.1 | 0.2 |
| AMJ553 | 3.2 | 0.1 |
| AMJ552 | 0.5 | 0.3 |
| AMJ551 | 0.4 | 0.1 |
| AMJ569 | 3.1 | 0.6 |
| AMJ568 | 1.3 | 0.1 |
| AMJ567 | 30 | 1.4 |
| AMJ566 | 18 | 1.1 |
| AMJ565 | 205 | 3 |
| AMJ577 | 48 | 3 |
| AMJ578 | 7 | 0.9 |
| AMJ579 | 0.6 | 0.8 |
| AMJ586 | 700 | 13 | pAMJ538 was constructed by exonuclease BAL31 deletions and comprises a 150 bp DNA fragment located immediately upstream the Tn917 insertion point in integrant strain PA170. No promoter activity was associated with this 150 bp DNA fragment.

To further define the 5' boundary of the promoter region, PCR was used to amplify *L. lactis* MG1363 chromosomal DNA fragments that covered 150 bp (primer 170-150), 160 bp (primer 170-160), 170 bp (primer 170-170), 180 bp (primer 170-180), and 190 bp (primer 170-190) upstream the insertion point, respectively (FIG. 2). These five gene specific primers, which all contain a XhoI restriction site in the 5' end, were used in combination with primer 170 BamHI. The amplified DNA fragments were subsequently digested with XhoI and BamHI and cloned into pAK80, generating pAMJ551, pAMJ552, pAMJ553, pAMJ554 and pAMJ561, respectively. The plasmids were introduced into *L. lactis* MG1363 and β-galactosidase activity assays (Miller, 1972) were performed on sets of cultures grown overnight in GM17 medium and ArgM17 medium, respectively. Based on the enzyme activity data (Table 1.1), the 5' end of the promoter region is located between bp No. 160 and bp No. 170 upstream of the Tn917 insertion point. pH regulation was intact for the clone comprising the 170 bp P170 DNA fragment.

The P170 promoter region was subsequently minimized from the 3' end by using an approach similar to that described above. Primers complementary to the DNA sequence located, respectively, 20 bp (primer 170 µl BamHI), 40 bp (primer 170 p2 10 BamHI), 60 bp (primer 170 p3 BamHI), 80 bp (primer 170 p4 BamHI), 100 bp (primer 170 p5 BamHI), 110 bp (primer 170 p6 BamHI), 120 bp (primer 170 p7 BamHI), and 130 bp (primer 170 p8 BamHI) upstream of the Tn917 insertion point were used in PCR reactions together with the primer 170—170 (FIG. 3). The PCR amplified L. lactis MG1363 chromosomal DNA fragments were digested with XhoI and BamHI and inserted into pAK80, generating the plasmids pAMJ569, pAMJ568, pAMJ567, pAMJ566, pAMJ565, pAMJ577, pAMJ578, and pAMJ579, respectively. The plasmids were introduced into L. lactis MG1363 and β-galactosidase activity assays were performed (Miller, 1972) on sets of cultures grown overnight in GM17 medium and ArgM17 medium, respectively (Table 1.1). The enzyme activities show that the 3' end of the promoter region is located between bp No. 120 and bp No. 130 upstream of the Tn917 insertion point.

The data show that a minimal promoter region able to direct gene expression comprises the DNA fragment extending from bp No. 120 to bp No. 170 upstream of the Tn917 point of insertion. This minimal promoter region is also regulatable by pH.

The *Lactococcus lactis* ssp. *cremoris* strains AMJ553 and AMJ567 were deposited under the Budapest Treaty on Sep. 4, 1996 with the German Collection of Microorganisms and Cell Cultures, Mascheroder Weg 1b, D-38124 Braunschweig, Germany under the accession Nos DSM 11135 and DSM 11136, respectively.

EXAMPLE 2
Construction of pAMJ586

Having created deletions from both ends of the P170 promoter region, pAMJ586 was constructed by creating an internal deletion in the P170 promoter region. A 190 bp DNA fragment corresponding to the sequence located upstream of the Tn917 insertion point in strain PA170 was PCR amplified using chromosomal DNA from L. lactis MG1363 as template and the primers 170-190 and 170 BamHI (FIG. 4). The amplified DNA fragment contains an internal HaeIII DNA fragment extending from bp No. 40 to bp No. 112 with respect to the Tn917 point of insertion. Digestion with HaeIII and BamHI and XhoI resulted in a mixture of fragments which were cloned into XhoI and BamHI digested vector pGEM7 Zf(+) (Promega), generating pAMJ146. pAMJ146 contains a 118 bp DNA fragment, indicating that the internal HaeIII fragment has been deleted. AMJ586 was constructed by cloning the 118 bp XhoI-BamHI DNA fragment from pAMJ146 into XhoI and BamHI digested pAK80. pAMJ586 was introduced into L. lactis MG1363 and β-galactosidase activity assays were performed (Miller, 1972) on sets of cultures grown overnight in GM17 medium and ArgM17 medium, respectively. The P170 derived promoter region on pAMJ586 generated a surprising and significant increase in β-galactosidase activity while still being regulatable by pH (Table 1.1).

The *Lactococcus lactis* ssp. *cremoris* strain AMJ586 was deposited under the Budapest Treaty on 4 September 1996 with the German Collection of Microorganisms and Cell Cultures, Mascheroder Weg 1b, D-38124 Braunschweig, Germany under the accession No. DSM 11137.

EXAMPLE 3
Fermentations of L. lactis strains AMJ553, AMJ567 and AMJ586

To study the promoter strength and regulation at fixed pH values, fermentations were performed with three selected L. lactis strains AMJ553, AMJ567, and AMJ586, corresponding to L. lactis MG1363 transformed with pAMJ553, pAMJ567, and pAMJ586, respectively. In one set of fermentors the pH was kept at 5.2 whereas pH in the other set of fermentors was kept at 7.0. At selected $OD_{600}$ values and time points, samples were collected for β-galactosidase activity assays and total RNA extraction for primer extension analysis. FIGS. 5, 6 and 7 show a representation of corresponding $OD_{600}$ values and β-galactosidase activities (Miller, 1972) for strains AMJ553, AMJ567, and AMJ586 respectively. It is clearly demonstrated that different levels of expression can be obtained by creating small alterations (deletions) in the P170 promoter region. The pH regulation is maintained for all three constructs.

EXAMPLE 4
Transcriptional analysis of the P170 promoter

The transcription start site of the P170 mRNA was determined by primer extension mapping. Primer lac-3, which is complementary to lacLM located downstream of the P170 derived promoter regions comprised in pAMJ553, pAMJ567 and pAMJ586, was end labelled with $\gamma^{32}$P-ATP using T4 polynucleotide kinase and annealed to 20 µg of total RNA isolated from cultures of AMJ553, AMJ567 and AMJ586 grown in flasks containing GM17 medium. Synthesis of cDNA was performed using the SuperScrip™ RNaseH⁻ Reverse Transcriptase (Life Technologies) as recommended by the supplier. These experiments revealed that mRNA transcription initiates at the G nucleotide positioned 114 bp upstream of the Tn917 insertion point. The mRNA transcription initiation site was identical for all three promoter constructs. However, the amount of detectable mRNA transcript varied among the constructs, indicating differences in production and/or stability of the transcripts.

Analysis of the putative promoter region directing gene expression in the pAK80 derivatives mentioned above revealed an extended –10 promoter region (Bidnenko et al., 1995) comprising the DNA sequence 5' CTAGTGC-TATAAT3' (SEQ ID NO:17) located in the region comprising bp No. 133-121 upstream of the Tn917 insertion point. No conceivable –35 region was identified, as expected for an extended –10 promoter. Open reading frames (ORF) could not be identified in the region located between the extended –10 promoter and the Tn917 insertion point, indicating that a putative ORF should be located downstream of the Tn917 insertion point.

EXAMPLE 5
Cloning the DNA sequence located downstream of the insertion point of integrant PA170 by Inverse PCR To confirm that the P170 promoter located on the chromosome of L. lactis MG1363 directs the expression of an open reading frame, inverse PCR (Madsen et al., 1996) was used to amplify the DNA sequence located downstream of the Tn917 insertion point of integrant PA170. Chromosomal DNA from L. lactis MG1363 was digested with DraI and RsaI, respectively, and the digestion mixtures were ligated. Two separate PCR reactions were performed using the primers pI1 and p170p3 (DraI digests) and pI1 and p170p5 (RsaI digest) (FIG. 8). The following temperature profile was used: Denaturation at 94° C., 30 sec.; annealing at 60° C., 30 sec.; extension at 72° C., 1 min. The total number of PCR cycles was 40 after which followed a single extension cycle at 72° C. for 10 min. The PCR amplification generated in both cases DNA fragments of approximately 1 kb, corresponding to the cloning of about 700 bp and 800 bp, respectively, downstream of the Tn917 insertion point in integrant PA170. The PCR products were purified and cloned into EcoRV digested pKS Bluescript II, resulting in plasmid pAMJ87 and pAMJ89. The cloned PCR products were sequenced (Table 5.1) and analysis of the DNA sequence revealed an ORF of 138 amino acids located 157 bp downstream of the Tn917 insertion point. The deduced amino acid sequence of this ORF is 57.3% identical to a hypothetical 14.6 kDa protein from *Bacillus subtilis* (Table 5.2). A putative ribosome binding site (5'GGAGG3') showing complementarity to the *L. lactis* 3' 16 S rRNA sequence (Chiaruttini and Milet, 1993) was identified 8 bp upstream of the translational start codon.

Table 5.1

DNA sequence downstream of the Tn917 insertion point in the integrant strain PA170 (SEQ ID NO:18). Also given is an open reading frame encoding a putative protein on 138 amino acids (SEQ ID NO:19)

(Linear) MAP of: 170down check: 5041 from:1 to:696

```
    GGAGCTTTTTTGTTTTGGGCAACTTGTTTTCTTCGTAATTTCTGTCAGTGGCTGATGATT
1   ---------+---------+---------+---------+---------+---------+   60

AAATGTTTTACTTTTCATTGCTCTAATCAGCTTCTCATAGGCAAATCAAATAAAGTCTGA
61  ---------+---------+---------+---------+---------+---------+  120

TATAACACTCAATAGCAAACATCGGAGGTAGATAGAATGCAAAACTTAGATTTAATCGAA
121 ---------+---------+---------+---------+---------+---------+  180
                                        M  Q  N  L  D  L  I  E

AATGAAATCAAAACAGTAATTGATACTTGTGACAAGTTAATCCATCAAGAAAAATTTGAT
181 ---------+---------+---------+---------+---------+---------+  240
     N  E  I  K  T  V  I  D  T  C  D  K  L  I  H  Q  E  K  F  D

GAATTGGTTAACTTTTATACTGAAGATGCCGTTTTAGTTATTAAACCTGGCATGCTCGCG
241 ---------+---------+---------+---------+---------+---------+  300
     E  L  V  N  F  Y  T  E  D  A  V  L  V  I  K  P  G  M  L  A

AATGGACGAGAACAAATTAAATCAGCTTTTATAAAAATTGCATCTTACTTTGATAATTCT
301 ---------+---------+---------+---------+---------+---------+  360
     N  G  R  E  Q  I  K  S  A  F  I  K  I  A  S  Y  F  D  N  S

ATTAAACCTCTTGAAGGAAAAATGGTTTATCTTCTTGCTGGTGATACCGTTCTTGTTTTG
361 ---------+---------+---------+---------+---------+---------+  420
     I  K  P  L  E  G  K  M  V  Y  L  L  A  G  D  T  V  L  V  L

GCTCAAACTTTTATTGAAGCAAACCAATCAGCAACTGCTCAGTCTGAATTTTCAATGGAG
421 ---------+---------+---------+---------+---------+---------+  480
     A  Q  T  F  T  E  A  N  Q  S  A  T  A  Q  S  E  F  S  N  E

AGAAGAGCAACTTATGTTTTTCGCAACATAGATGGAAAATGGTTATGTGCAATTGATAAT
481 ---------+---------+---------+---------+---------+---------+  540
     R  R  A  T  Y  V  F  R  N  I  D  G  K  W  L  C  A  I  D  N

TCTTATGGGACAACTCTTATTGACGAAAAATAAAATAGAAAGCTATACTTACAACTTCAT
541 ---------+---------+---------+---------+---------+---------+  600
     S  Y  G  T  T  L  I  D  E  K  *   (SEQ ID NO:19)

TGAGGTTCTTTTTTACTTTAATTATTATTTATTTTATCTCTTTATTCTTCCTTTTTCATC
601 ---------+---------+---------+---------+---------+---------+  660

CCTACCCATTTTTTTAGATCTTACTTCAATTTTAAA     (SEQ ID NO: 18)
661 ---------+---------+----------+----- 696
```

Table 5.2.

Homology search (Fasta) using the putative protein of 138 amino acids (170dow: SEQ ID NO:19; yybh b: SEQ ID NO:20)

```
(Peptide) FASTA of: 170down.pep from:1 to: 138 September 2, 1996
17:11

TRANSLATE of: 170down check: 5041 from: 157 to 572
generated symbols 1 to: 138.

TO: asw:* Sequences: 53,319 Symbols: 18,959,537 Word Size:2
Scoring matrix: GenRunData: fastapep.cmp
Variable pamfactor used
Gap creation penalty: 12.0 Gap extension penalty: 4.0

170down.pep
sw:yybh_bacsu

ID   YYBH_BACSU   STANDARD;   PRT;   129 AA.
AC   P37496;
DT   01-OCT-1994   (REL. 30, CREATED)
DT   01-OCT-1994   (REL. 30, LAST SEQUENCE UPDATE)
DT   01-FEB-1995   (REL. 31, LAST ANNOTATION UPDATE)
DE   HYPOTHETICAL 14.6 KD PROTEIN IN COTF-TETB INTERGENIC REGION.

SCORES Init1: 262  Initn: 371  Opt: 422
       57.3% identity in 131 aa overlap
                10         20         30         40         50         60
170dow  MQNLDLIENEIKTVIDTCDKLIHQEKFDELVNFYTEDAVLVIKPGMLANGREQIKSAFIK
        :|:::|::|::||   |::|:||:|:|:|:|||||:|||:|:|:|:||:|||:
yybh_b      MEQQLKDIISACDLAIQNEDFDTLMNYYSEDAVLVVKPGMIARGKEEIKKAFIT
                10         20         30         40         50
                70         80         90        100        110        119
170dow  IASYFDNSIKPLEGKNVYLLAGDTVLVLAQTFIEANQSATAQSEFSMERRATYVF-RNID
        ||:||::|  |  :|||:  |  ||||||||:||:::::::   :||::|||||||| :| :
yybh_b  IANYFNHHIVPTQGHMILLEAGDTVLVLSQTLLDSDKK---DSEYAMERRATYVFKKNAQ
                60         70         80         90        100        110

120        130
170dow  GKWLCAIDNSYGTTLIDEK   (SEQ ID NO:19)
        |:|||:|||||||:||:
yybh_b  GEWLCVIDNSYCTDLICV    (SEQ ID NO:20)
                120
```

EXAMPLE 6
Construction of a series of pH regulatable gene expression/secretion vectors for *L. lactis* based on the P170 promoter regions comprised in pAMJ553, pAMJ567 and pAMJ586

A set of pH regulatable expression/secretion vectors was constructed by combining different P170 derivatives with DNA encoding the Usp translocation signal peptide contained in plasmid pNZ1020 (received from NIZO, van Asseldonk et al., 1990, GenBank M35374). Essentially, the open reading frame of the lacLM cassette were deleted from the vectors pAMJ553, pAMJ567, and pAMJ586 and replaced by a novel PCR generated gene cassette containing DNA fragments encoding the Usp signal peptide, including the cleavage site for the signal peptidase, followed by a multiple cloning site. The Usp signal sequence was generated by using pNZ1020 as a template in a PCR reaction with primers designated Usp primer 1 and Usp primer 2. Usp primer 1 is complementary to the DNA sequence comprising the unique BamHI site and the ATG start codon of lacLM on pAK80, and by the first 23 bp of the Usp45 signal sequence. Usp primer 2 is complementary to the four codons located immediately upstream of, and the two codons located immediately downstream of the signal peptidase cleavage site, followed by a multiple cloning site that includes BglII, PstI and SalI sites. The PCR generated DNA fragment comprises the ribosome binding site of lacLM followed by the first 29 codons of the 5' end of the Usp signal sequence and a multiple cloning site. The generated 158 bp PCR product was digested with BamHI and SalI and ligated into pAMJ553, PAMJ-567, and pAMJ586, respectively, which had been digested with BamHI and SalI. After transformation into *E. coli*, plasmid DNA was purified and each construction was verified by DNA sequencing. The resulting vectors, facilitating pH regulatable expression of genes of interest, followed by secretion of the gene products to the culture medium, were termed pSMA607, pSMA609, and pSMA610, respectively.

Additionally, three vectors, pSMA604, pSMA605, and pSMA606 were constructed. These vectors correspond to pSMA607, pSMA609, and pSMA610, the only difference being a lack of the DNA encoding the signal peptide. Consequently, these vectors are suited for the production of proteins intended to end up inside the lactic acid bacteria. Essentially, the vectors were constructed by cloning a PCR fragment containing the sequence between the unique BamHI site and the ATG start codon of lacLM, followed by a multiple cloning site into the vectors pAMJ553, pAMJ567, and pAMJ586, respectively. The ATG codon is included in the constructions.

EXAMPLE 7
Application of the vectors pSMA607, pSMA609, and pSMA610 for pH regulatable expression and secretion of the *Staphylococcus aureus* nuclease (SNase) in *L. lactis*

To demonstrate the potential of using P170 promoter derivatives for pH regulatable expression and subsequent secretion of a heterologous gene, the gene coding for S. aureus nuclease (SNase) was selected as a model gene. SNase has been cloned and expressed in several microorganisms including L. lactis (Le Loir et al., 1994). SNase is a small and well cha- racterized enzyme, that is secreted by S. aureus either as a polypeptide of 168 amino acids or as a derivative lacking the first 19 N-terminal amino acids. The SNase is synthesized as a pro-form comprising a signal peptide of 60 amino acids. To clone and express the SNase without its native expression signals and signal peptide, two primers were designed, Nuc1 and Nuc2, that facilitated PCR amplification of a 567 bp DNA fragment including the coding sequence corresponding to the 168 C-terminal amino acids and 63 bp downstream of the translational stop codon. Plasmid pBS::nuc (Le Loir et al., 1994) contains the entire SNase gene on an 871 bp EcoRI DNA fragment and was used as template in a PCR reaction with the primers Nuc1 and Nuc2, which contain a BglII and a SalI site in the 5' end, respectively, facilitating subsequent cloning into the vectors pSMA607, pSMA609, and pSMA610. BglII and SalI digested PCR fragments were ligated with pSMA607, pSMA-609, and pSMA610 digested with BglII and SalI. After transformation of the ligation mixture into E. coli, plasmid DNA was purified and the constructs were verified by DNA sequencing. The verified constructs were transformed into L. lactis MG1363, generating strains AMJ638, AMJ626, and AMJ627. A plasmid, pSMA614, containing the entire nuclease gene and its native expression signals including DNA encoding the signal peptide was constructed by inserting a 0.9 kb XhoI-BamHI fragment from pBS::nuc into pAK80.

EXAMPLE 8

Plate assay for detection of SNase activity in L. lactis

The strains AMJ638, AMJ626, and AMJ 627 were tested for extracellular SNase activity by placing 50 µl supernatant from overnight cultures grown in GM17 and ArgM17, respectively into wells of DNA-agar plates containing Toluidine Blue O (TB). SMA614 was used as a nuclease positive control, whereas AMJ648 harbouring pSMA610 was used as a nuclease negative control. The plates were incubated at 37° C. for 18 hours and pink haloes were observed around the wells containing supernatant from strains producing an active, secreted SNase. The diameter of the haloes corresponded to the expected promoter strength. Expressions were found to be pH regulated.

EXAMPLE 9

Production of SNase using strain AMJ627

To analyse the production potential for SNase in L. lactis, we performed fermentations of strain AMJ627 at fixed pH values of 5.2 and 7.0, respectively. AMJ648 was used as a nuclease negative control. As previously described (Israelsen et al., 1995), samples were collected from each fermentation at selected $OD_{600}$ values and time points for measuring nuclease activity quantitatively.

Culture supernatants were separated from the cells by centrifugation. Nuclease activity in the supernatants was determined by incubation with sonicated salmon DNA as substrate followed by precipitation in ice-cold perchloric acid and subsequent measurement of absorbance at 260 nm ($A_{260}$) in the supernatant. The assay procedure was as follows: 10 µl of sample was added to 500 µl of reaction buffer (1 mg/ml DNA, 0.1 mg/ml Bovine Serum Albumin, 10 mM $CaCl_2$, 25 mM Tris-HCl pH 8,8) and incubated at 37° C. After 30 minutes, 500 µl of ice-cold 4% (w/v) perchloric acid was added. The larger DNA fragments were allowed to precipitate for 15 to 30 minutes at 0° C. and finally separated from the acid soluble degradation products by centrifugation. $A_{260}$ in the supernatant was measured in a 1 cm light path. To obtain the $A_{260}$ corresponding to "time zero" for each sample, 500 µl reaction buffer was mixed with 500 µl 4% PCA at 0° C, 10µl sample was added and precipitation performed as described above. One unit of nuclease is defined as the amount of active nuclease that will produce 1 µmole of acid soluble polynucleotides from native DNA per minute. The SNase activity in units per ml sample is obtained from $\Delta A_{260}$ by the formula:

$$\frac{[A_{260}(30 \text{ min}) - A_{260}(0 \text{ min})] \cdot 1.01 \cdot 100}{10 \cdot 30}$$

where the number 10 is the millimolar extinction coefficient at 260 nm for mixed nucleotides and 1.01 is the final volume in ml. To obtain a $\Delta A_{260}$ within a suitable range, we diluted high activity samples to 0.1–0.25 units/ml before assaying the activity. Micrococcal Nuclease from Staphylococcus aureus (Sigma Chemical Company, N 5386) was used as a standard.

In FIG. 9, the activities and cell densities obtained during fermentation of AMJ627 are shown versus time. Assuming that the specific activity of the enzyme produced by AMJ627 was the same as that given for the Sigma nuclease (135 units/mg protein), we have estimated the amount of SNase protein produced by the strain during the fermentations. 15 µg/ml at $OD_{600}$=3 was obtained under induced conditions (pH 5.2), while 0.2 µg/ml at $OD_{600}$=3 was obtained under repressed conditions (pH 7.0).

EXAMPLE 10

Modulation of the expression level conferred by a regulatable promoter by point mutations in the promoter region From the above deletion analyses it is evident that the expression level conducted by P170 can be highly modulated by creating small deletions in the region located between the original insertion point in the transposon integrant PA170 (position 1) and the transcriptional start site (position 114) (Example 1).

In order to mutate and thereby identify single bases involved in this modulation, hydroxylamine was used for chemical mutagenesis. Hydroxylamine reacts with the pyrimidines of DNA and probably only its reaction with cytosine is mutagenic, resulting in C to T transitions, i.e C-G base pairs are changed to T-A base pairs in the DNA double helix. As target for the mutagenesis, plasmid pAMJ553 (Example 6) was selected. pAMJ553 contains 170 bp located immediately upstream the original insertion point, transcriptionally fused to the lacLM reporter gene of pAK80.

Five µg plasmid DNA dissolved in 20 µl TE buffer (10 mM Tris, 1 mM EDTA, pH 7.6) was mixed with 100 µl of sodium phosphate buffer (0.1 M, pH 6.0) containing 1 mM EDTA. Following addition of 80 µl hydroxylamine (1 M, pH adjusted to 6.0 with NaOH) the mixture was incubated at 70° C. for 2 hours. The DNA was extracted twice with phenol, precipitated with ethanol and dissolved in 10 µl TE buffer.

250 ng mutagenized plasmid DNA was introduced into L. lactis MG1363 by electroporation as described above (Example 6).

Transformants were selected on SGM17 agar plates supplemented with 1 µg/ml erythromycin and 160 µg/ml of the chromogenic substrate 5-bromo-4 chloro-3-indolyl-β-D-galactopyranoside (X-gal). 20 transformants showing varying intensity of blue colour as compared to the wildtype strain, AMJ553, were isolated and restreaked onto GM17 plates containing erythromycin and X-gal in the above-mentioned concentrations.

To locate the position of mutation(s) in the 20 selected mutants, the 170 bp promoter fragment from each mutant was PCR amplified and sequenced by use of the solid phase sequencing kit from Pharmacia. 14 mutants contained wild-type DNA sequence in the 170 bp region, whereas the six remaining mutants contained four different types of point mutations. Both mutants containing single or double point mutations were identified. FIG. 10 shows the positions of the identified mutations.

The 170 bp DNA fragment from each of the four different mutants were subcloned into the promoter probe vector pAK80 to verify that the identified mutations were responsible for the observed phenotype. β-Galactosidase activity measurement was subsequently performed as described in Example 1 on cultures which were grown overnight in GM17 or ArgM17 medium, respectively (Table 10.1).

TABLE 10.1

β-Galactosidase activity (Miller units) in L. lactis MG1363 strains grown overnight in GM17 (pH 5.5 after growth) or ArgM17 (pH 7.0 after growth)

| L. lactis MG1363, containing plasmid | β-Galactosidase activity GM17 | ArgM17 |
|---|---|---|
| pAMJ553 (wildtype) | 1.9 | 0.1 |
| pMut1 | 27 | 1.9 |
| pMut2 | 25 | 1.5 |
| pMut20 | 0.8 | 0.2 |
| pMut56 | 0.8 | 0.2 |

The results presented in FIG. 10 and Table 10.1 clearly demonstrate that single base substitutions in the region located between the transcriptional start site and the original transposon insertion point can modify the induced expression level conferred by the P170 promoter. Two types of mutations were found to increase the expression level: the substitution of cytosine at position 61 with a thymine in mutant No. 1 and 3 and the double substitution of cytosine at positions 61 and 69 with thymine in mutants No. 2 and 59. Two other types of mutations were found to decrease the induced expression level: the substitution of cytosine at position 80 with a thymine in mutant No. 20 and the double substitution of cytosine at positions 69 and 80 with thymine in mutant No. 56.

The P170 expression was found to be regulated by pH in the tested mutants.

The results in this example also indicate that the variation of expression levels obtained in the deletion analysis (Example 1) is a consequence of increasing/decreasing the activity of a functional element that affects the readthrough or stability of the transcript.

EXAMPLE 11

Cloning and expression of two Mycobacterium tuberculosis antigens, MPT64 and ESAT-6, in the secretion vector pSMA610.

In this Example is described the cloning and expression of two Mycobacterium tuberculosis antigens using the pH regulated secretion vector pSMA610. The two antigens are proteins found in short-term culture filtrates of M. tuberculosis. The antigens are of potential use as diagnostic skin test reagents and as components in subunit vaccines directed against tuberculosis.

1. Cloning of the MPT64 antigen

The DNA sequence encoding the mature secreted antigen MPT64 (205 amino acids, 22.4 kDa) (Oettinger and Andersen, 1994) from the *M. tuberculosis* H37Rv (ATCC 27294) strain was amplified using PCR technique. The primers mpt64 p3 (5' TTTCTGCTGCAGCCCCGTTGT-CAGGTGTTTACGCTGCGCCCAAGACCTACTGCGAG 3') (SEQ ID NO:21) and mpt64 p2 (5' ACGCGTCGAC-CTAGGCCAGCATCGAGTC 3') (SEQ ID NO:22) were used in a PCR reaction with chromosomal DNA from *M. tuberculosis* H37Rv as template (the PstI and SalI restriction sites in the primers are underlined). Following digestion with PstI and SalI, the amplified DNA fragment was ligated into the PstI and SalI sites of the secretion vector pSMA610, resulting in plasmid pAMJ715. This cloning was designed to obtain a fusion of the 27 N-terminal amino acids of Usp45, encoding a signal peptide, to the N-terminal of the mature MPT64 antigen.

The primary protein structure of the MPT64 antigen secreted from *L. lactis* MG1363 containing plasmid pAMJ715 should be identical to the primary protein structure of MPT64 found in short-term filtrates of *M. tuberculosis* strain H37Rv. Plasmid pAMJ715 was introduced into *L. lactis* and the resulting strain was named AMJ715.

2. Cloning of ESAT-6

Using the same approach as described above, another secreted antigen, ESAT-6 (95 amino acids, 6 kDa) (Sorensen et al., 1995) from *M. tuberculosis* strain H37Rv, was PCR amplified and inserted into the secretion vector pSMA610. The two primers MT ESAT-6-3 (5'GGAAGATCTATGACAGAGCAGCAGTGG 3') (SEQ ID NO:23) and MT ESAT-6-2 (5'ACGCGTCGACCTATGCGAACATCCC 3') (SEQ ID NO:24) were used in a PCR reaction with chromosomal DNA from *M. tuberculosis* H37Rv as template (the BglII and SalI restriction sites in the primers are underlined). The generated PCR fragment was digested with BglII and SalI and ligated into pSMA610, predigested with BglII and SalI, yielding plasmid pAMJ700.

Plasmid pAMJ700 was introduced into *L. lactis* resulting in strain AMJ700. Strain AMJ700 was designed to secrete an ESAT-6 antigen containing four artificial amino acids in the N-terminal of the antigen, originating from the multiple cloning site of pSMA610.

In another construction, two copies of the ESAT-6 gene were inserted in tandem into the secretion vector pSMA610. This was done by insertion of another copy of ESAT-6 into vector pAMJ700 that already contained one copy of the ESAT-6 gene. The second ESAT-6 gene copy was produced using the primers MT ESAT-6-3 and MT ESAT-6-4 (5' GGAAGATCTTGCGAACATCCCAGTG 3') (SEQ ID NO:25). MT ESAT-6-4 contains a BglII restriction site (underlined) and is complementary to the C-terminal of ESAT-6 except for the lack of a stop codon. After PCR amplification, the DNA fragment was digested with BglII and inserted into pAMJ700 which was predigested with BglII. A plasmid containing two ESAT-6 gene copies inserted in the correct orientation was obtained and named pAMJ717. Plasmid pAMJ717 was designed to encode a secreted polypeptide composed of four artificial N-terminal amino acids, originating from the multiple cloning site followed by two ESAT-6 copies. pAMJ717 was introduced into *L. lactis* resulting in strain AMJ717.

3. Fermentation of *L. lactis* strains AMJ700. AMJ715 and AMJ717 expressing mycobacterial antigens.

Strain AMJ700, AMJ715 and AMJ717 were pre-propagated in GM17 medium supplemented with 1 μg/ml erythromycin. 10 ml overnight culture of each strain was inoculated into separate fermentors, each containing 1 liter SAIV medium (Jensen and Hammer, 1993) supplemented with 1 μg/ml erythromycin. The incubation temperature was kept at 30° C. with constant stirring at 300 rpm. The pH value was monitored and a set point of 5.2 was kept by titrating with 1 M NaOH. The pH set point was reached after 6–8 hours of growth and after additional 4 hours of incubation, samples were collected for analysis of antigen production in each strain.

The cell pellet was removed by centrifuging the cultures at 3000×g for 10 min. The supernatants were prepared for further analysis by concentrating 40 times using the microfiltration system available from Amicon and Millipore.

4. Detection and quantification of mycobacterial antigens produced in L. lactis by SDS-PAGE and western blotting.

Concentrated culture supernatants from strain AMJ700, AMJ715 and AMJ717 were boiled in sample buffer (Novex) containing 5% DTT prior to loading onto 16% tricine polyacrylamide SDS-gels (Novex). Samples were subjected to electrophoresis and the gels were stained with colloidal Coomassie Blue using the protocols recommended by Novex.

Proteins were electroblotted onto a nitrocellulose membrane (Novex) using the Novex mini-tank blotter for 1.5 hours with a constant power of 50 Volts. The membrane was blocked for 5 min. in TBS buffer (50 mM Tris-base pH 10.2, 500 mM NaCl) containing 5% BSA, washed once in TBS buffer containing 0.05% Tween-20 and 0.1% BSA. The membrane was subsequently incubated overnight with the primary antibody corresponding to the respective antigens. Monoclonal antibodies HYB76-8 (Klausen et al., 1994) directed against ESAT-6, and C24b1 (Andersen et al., 1991) directed against MPT64 were used at a dilution of 1:500 in TBS buffer containing 0.05% Tween-20 and 0.1% BSA. The membranes were washed three times for 5 minutes in the same buffer as used for primary antibody incubation. The secondary rabbit anti-mouse AP-conjugated antibody (DAKO) was diluted 1:2000 and incubated with the membrane for 2 hours at the same conditions as for the primary antibody. The previous washing conditions were introduced and finally the nitrocellulose membrane was developed using the NBT/BCIP Ready-to-Use tablets as recommended by the manufacturer (Boehringer Mannheim).

FIG. 11 shows a SDS-PAGE (left) and the corresponding western blot (right) obtained from strain AMJ715 expressing MPT64. The SDS-PAGE shows a major distinct band of about 30 kDa; a protein band hybridizing at the same position in the western blot analysis confirms the identity of MPT64. MPT64 has been described to migrate at a position corresponding to 24 kDa (Oettinger et al., 1995). This discrepancy might be caused by the 16' tricine gels used in this study, as the native MPT64 from short-term filtrates of M. tuberculosis migrates at the same position (data not shown). Based on the amount of MPT64 antigen found in short-term filtrates (about 5%), the secreted amount of MPT64 antigen in L. lactis strain AMJ715 is estimated to 10–15 mg/l.

FIG. 12 shows a SDS-PAGE (left) and the corresponding western blot (right) obtained from strain AMJ700 expressing a single copy of ESAT-6. No obvious protein band could be identified on the Coomassie stained gel, but using a monoclonal ESAT-6 antibody, two major products at 6 kDa were visible. The same pattern was observed in short-term culture filtrates from M. tuberculosis expressing ESAT-6 (Sorensen et al., 1995). In order to quantify the amount of secreted ESAT-6 antigen, a recombinant ESAT-6 protein of known concentration produced in E. coli at Statens Seruminstitut Denmark (unpublished data), was used as standard. The protein produced by E. coli contains 24 artificial amino acids in the N-terminal due to a histidine tag and a multiple cloning site. Therefore the calculation is only semi-quantitative. Estimated from scanning the western blot, the secreted level of ESAT-6 antigen from strain AMJ700 was less than 5 mg/l.

FIG. 13 shows a SDS-PAGE (left) and a western blot (right) of supernatant from strain AMJ717 expressing two ESAT-6 gene copies in tandem. On the SDS-PAGE a dominant band having a molecular weight of about 30 kDa was identified. Western blot analysis confirmed the identity of this band as having ESAT-6 epitopes. Using recombinant E. coli produced ESAT-6 protein as standard, the amount of secreted ESAT-6-ESAT-6 protein from strain AMJ717 was estimated to be in excess of 30 mg/l.

From the examples described above it is clearly demonstrated that the secretion vector pSMA610 is capable of expressing heterologous genes and subsequently direct the gene products to the external growth medium. The amount of secreted protein is variable, ranging from less than 5 mg/l to levels exceeding 30 mg/l. These differences might be caused by different chemical or physical characteristics of the individual heterologous proteins. The activity of the P170 promoter in the chemically defined media SAIV was also demonstrated. This activity is important due to the fact that many pharmaceutical proteins are not allowed to be produced in complex media containing animal proteins.

REFERENCES

1. Alexieva, Z., E. J. Duvall, N. P. Ambulos, Jr., U. J. Kim, and P. S. Lovett. 1988. Chloramphenicol induction of cat-86 requires ribosome stalling at a specific site in the regulatory leader. Proc. Nat. Acad. Sci. USA 85:3057–3061.
2. Andersen, Å. B., L. Ljungquist, K. Haaslov and M. W. Bentzon. 1991. MPT64 possesses "tuberculosis-complex"-specific B- and T-cell epitopes. Scand. J. Immunol. 34:365–372.
3. Bidnenko, E., D. Ehrlich, and M. -C. Chopin. 1995. Phage operon involved in sensitivity to the Lactococcus lactis abortive infection mechanism AbiD1. J. Bacteriol. 177:3824–3829.
4. Chiaruttini, C. and M. Milet. 1993. Gene organization, primary structure and RNA processing analysis of a ribosomal RNA operon in Lactococcus lactis. J. Mol. Biol. 230:57–76.
5. David, S., H. Stevens, M. van Riel, G. Simons and W. M. de Vos. 1992. Leuconostoc lactis β-galactosidase is encoded by two overlapping genes. J. Bacteriol. 174:4475–4481.
6. de Ruyter, P. G. G. A., O. P. Kuipers, M. M. Beerthuyzen, I. van Alen-Boerrigter, and W. M. de Vos. 1996. Functional analysis of promoters in the nisin gene cluster of Lactococcus lactis. J. Bacteriol. 178:3434–3439.
7. Gasson, M. J. 1983. Plasmid complements of Streptococcus lactis NCDO 712 and other lactic streptococci after protoplast-induced curing. J. Bacteriol. 154:1–9.
8. Hanahan, D. 1983. Studies on transformation of Escherichia coli with plasmids. J. Molec. Biol. 166:557–580.
9. Holo H., and I. F. Nes. 1989. High-frequency transformation, by electroporation, of Lactococcus lactis subsp. cremoris grown with glycine in osmotically stabilized media. Appl. Environ. Microbiol. 55:3119–3123.
10. Israelsen, H. and E. B. Hansen. 1993. Insertion of transposon Tn917 derivatives into the Lactococcus lactis subsp. lactis chromosome. Appl. Environ. Microbiol. 59: 21–26.
11. Israelsen, H., S. M. Madsen, A. Vrang, E. B. Hansen, and E. Johansen. 1995. Cloning and partial characterization of regulated promoters from *Lactococcus lactis* Tn917-lacZ with the new promoter probe vector, pAK80. Appl. Environ. Microbiol. 61: 2540–2547.
12. Jahns, A., A. Schafer, A. Geiss and M. Teuber. 1991. Identification, cloning and sequencing of the replication region of *Lactococcus lactis* subsp. *lactis* biovar. *diacetylactis* Bu2 citrate plasmid pSL2. FEMS Microbiol. Lett. 80:253–258.
13. Jensen, P. and K. Hammer. 1993. Minimal requirement for exponential growth of *Lactococcus lactis*. Appl. Environ. Microbiol. 59:4363–4366.
14. Johansen, E., and A. Kibenich. 1992. Characterization of Leuconostoc isolates from commercial mixed strain mesophilic starter cultures. J. Dairy Sci. 75:1186–1191.
15. Kiewiet, R., J. Kok, J. F. M. L. Seegers, G. Venema and S. Bron. 1993. The mode of replication is a major factor in segregational plasmid instability in *Lactococcus lactis*. Appl. Environ. Microbiol. 59:358–364.
16. Klausen, J., M. Magnusson, A. B. Andersen, and C. Koch. 1994. Characterization of purified protein derivative of tuberculin by use of monoclonal antibodies: isolation of a delayed-type hypersensitivity reactive component from *Mycobacterium tuberculosis* filtrate. Scand. J. Immunol. 40:345–349.
17. Le Loir, Y., A. Gruss, S. D. Ehrlich, and P. Langella. 1994. Direct screening of recombinants in Gram-positive bacteria using the secreted Staphylococcal nuclease as a reporter. J. Bacteriol. 176:5135–5139.
18. Macrina, F. L., R. P. Jones, J. A. Tobian, D. L. Hartley, D. B. Clewell and K. R. Jones 1983. Novel shuttle plasmid vehicles for Escherichia-Streptococcus transgeneric cloning. Gene 25:145–150.
19. Madsen, S. M., B. Albrechtsen, E. B. Hansen, and H. Israelsen. 1996. Cloning and transcriptional analysis of two threonine biosynthetic genes from *Lactococcus lactis* MG1614. J. Bacteriol. 178:3689–3694.
20. Maniatis, T., E. F. Fritsch, and J. Sambrook. 1982. Molecular cloning: a laboratory manual. Cold Spring Harbor Laboratory, Cold Spring Harbor, N.Y.
21. Marsh, J. L., M. Erfle and E. J. Wykes. 1984. The pIC plasmid and phage vectors with versatile cloning sites for recombinant selection by insertional inactivation. Gene 32:481–485.
22. Miller, J. H. 1972. Experiments in Molecular Genetics. Cold Spring Harbor Laboratory, Cold Spring Harbor, N.Y.
23. Nauta, A., D. van Sinderen, H. Karsens, E. Smit, G. Venema, and J. Kok. 1996. Inducible gene expression mediated by a repressor-operator system isolated from *Lactococcus lactis* bacteriophage r1t. Mol. Microbiol. 19:1331–1341.
24. Oettinger, T. Å. B. Andersen. 1994. Cloning and B-cell epitope mapping of MPT64 from *Mycobacterium tuberculosis* H37Rv. Infect Immun. 62:2058–2064.
25. Oettinger, T., A. Holm., I. M. Mtoni,. Å. B. Andersen, and K. Haasløv. 1995. Mapping of the delayed-type hypersensitivity-inducing epitope of secreted protein MPT64 from *Mycobacterium tuberculosis*. Infect Immun. 63: 4613–4618.
26. O'Sullivan, D. J., S. A. Walker, S. G. West, and T. R. Klaenhammer. 1996. Development of an expression strategy using a lytic phage to trigger explosive plasmid amplification and gene expression. Biotechnology 14:82–87.
27. Pedersen, M. L., K. R. Arnved and E. Johansen. 1994. Genetic analysis of the minimal replicon of the *Lactococcus lactis* subsp. *lactis* biovar *diacetylactis* citrate plasmid. Mol. Gen. Genet. 244:374–382.
28. Simons, G., H. Buys, E. Koenhen and W. M. De Vos. 1990. Construction of a promoter-probe vector for lactic acid bacteria using the lacG gene of *Lactococcus lactis*. In: Developments in Industrial Microbiology, Supplementum 5, 31:31–39.
29. Steidler, L., J. M. Wells, A. Raeymaekers, J. Vandekerckhove, W. Fiers, and E. Remaut. 1995. Secretion of Biologically active murine interleukin-2 by *Lactococcus lactis* subsp. *lactis*. Appl. Environ. Microbiol. 61:1627–1629.
30. Sørensen, A. L., S. Nagai, G. Houen, P. Andersen and A. B. Andersen. 1995. Purification and characterization of a low-molecular-mass T-cell antigen secreted by *Mycobacterium tuberculosis*. Infect Immun. 63: 1710–1717.
31. van Asseldonk, M., G. Rutten, M. Oteman, R. J. Siezen, W. M. de Vos, and G. Simons. 1990. Cloning of usp45, a gene encoding a secreted protein from *Lactococcus lactis* subsp. *lactis* MG1363. Gene 95:155–160.
32. van Asseldonk, M., A. Simons, H. Visser, W. M. de Vos, and G. Simons. 1993. Cloning, nucleotide sequence, and regulatory analysis of the *Lactococcus lactis* dnaJ gene. J. Bacteriol. 175:1637–1644.
33. van der Vossen, J. M. B. M., D. van der Lelie and G. Venema. 1987. Isolation and characterization of *Lactococcus lactis* subsp. *cremoris* Wg2-specific promoters. Appl. Environ. Microbiol. 53:2452–2457.
34. van der Vossen, J. M. B. M., J. Kok and G. Venema. 1985. Construction of cloning, promoter-screening, and terminator-screening shuttle vectors for *Bacillus subtilis* and *Lactococcus lactis* subsp. *lactis*. Appl. Environ. Microbiol. 50:540–542.
35. van Rooijen, R. J., M. J. Gasson, and W. M. de Vos. 1992. Characterization of the *Lactococcus lactis* lactose operon promoter: Contribution of flanking sequences and LacR repressor to promoter activity. J. Bacteriol. 1742273–2280.
36. Wells, J. M., P. W. Wilson, P. M. Norton, M. J. Gasson, and R. W. F. Le Page. 1993a. *Lactococcus lactis:* High level expression of tetanus toxin fragment C and protection against lethal challenge. Mol. Microbiol. 8:1155–1162.
37. Wells, J. M., P. W. Wilson, P. M. Norton, M. J. Gasson, and R. W. F. Le Page. 1993b. A model system for the investigation of heterologous protein secretion pathways in *Lactococcus lactis*. Appl. Environ. Microbiol. 59:3954–3959.

What is claimed is:

1. An expression vector capable of being replicated in a lactic acid bacterial cell, said vector comprising:
   (i) a promoter region comprising: (a) a promoter element, wherein the function of the promoter element is regulatable by a factor selected from the group consisting of pH, growth temperature, oxygen content, a temperature shift eliciting the expression of heat shock genes, growth medium composition, including the ionic strength and NaCl content, the presence of essential cell constituents or precursors therefor, the growth phase of the bacterium and the growth rate of the bacterium and (b) at least one further nucleotide element, wherein the sequence of said nucleotide element affects the expression of a gene operably linked to the promoter region, and
   (ii) at least one restriction site,
      wherein the sequence of at least one of said elements (a) or (b) is modified relative to the sequence of the corresponding non-modified element,
      and further wherein said modification increases the expression level of a gene operably linked to the promoter region by at least two-fold, relative to the expression level, under essentially identical environmental conditions, of the same gene under the control of the corresponding non-modified promoter region,
      and further wherein the regulation of the promoter by said factors is not reduced or eliminated by said modification.

2. A vector according to claim 1 wherein the promoter region is derived from a lactic acid bacterium.

3. A vector according to claim 2 wherein the promoter region is derived from *Lactococcus lactis*.

4. A vector according to claim 1 wherein the gene expression is increased at least ten-fold.

5. A vector according to claim 1 which comprises a gene which is operably linked to the promoter region.

6. A vector according to claim 5 wherein the gene is a heterologous gene.

7. A vector according to claim 5 which comprises a signal sequence.

8. A vector according to claim 5 wherein the gene is one coding for a biologically functional gene product selected from the group consisting of an enzyme including an enzyme which regulates the formation of a flavoring compound, a toxin, an immunologically active polypeptide, a pharmaceutically active polypeptide and an antimicrobially active polypeptide.

9. A vector according to claim 5 wherein the gene is a gene coding for a mycobacterial oligo- or polypeptide.

10. A lactic acid bacterium which is transformed with the vector of claim 9.

11. A lactic acid bacterium according to claim 10 which is *Lactococcus lactis*.

12. A vector according to claim 1 which is selected from the group consisting of pAMJ553, pAMJ567 and pAMJ586 which are deposited under the accession numbers DSM 11135, DSM 11136 and DSM 11137, respectively.

13. A lactic acid bacterium which is transformed with a vector according to claim 1.

14. A lactic acid bacterial starter culture comprising cells of claim 13.

15. A starter culture according to claim 14 comprising a mixture of separate cell strains, the expression of the gene coding for a gene product being altered differently in each separate strain.

16. A lactic bacterium according to claim 13 wherein the vector or elements hereof is integrated into the chromosome.

17. A lactic acid bacterium according to claim 13 which is selected from the group consisting of Lactococcus spp., Streptococcus spp., Enterococcus spp., Lactobacillus spp., Leuconostoc spp., Pediococcus spp., Brevibacterium spp., Propionibacterium spp. and Bifidobacterium spp.

18. A lactic acid bacterium according to claim 17 wherein the lactic acid bacterium is *Lactococcus lactis*.

19. An expression vector comprising:
   a promoter operably linked to a gene encoding a protein of interest,
      wherein said promoter comprises a polynucleotide having the sequence of SEQ ID NO: 26.

20. An expression vector comprising:
   a promoter operably linked to a gene encoding a protein of interest, wherein said promoter comprises a polynucleotide having the sequence of SEQ ID NO: 29.

21. An expression vector comprising:
a promoter operably linked to a gene encoding a protein of interest,
wherein said promoter comprises a polynucleotide having the sequence of SEQ ID NO: 30.

22. An expression vector comprising:
a promoter operably linked to a gene encoding a protein of interest,
wherein said promoter is a XhoI-BamH1 restriction fragment derived from the pAMJ567 plasmid contained in the *Lactococus lactis* ssp. *cremoris,* deposited under accession number DSM 11136.

23. An expression vector comprising:
a promoter operably linked to a gene encoding a protein of interest,
wherein said promoter is a XhoI-BamH1 restriction fragment derived from the pAMJ586 plasmid contained in the *Lactococus lactis* ssp. *cremoris,* deposited under accession number DSM 11137.

24. A recombinant lactic acid bacterial cell comprising the following operably linked elements, wherein the position, orientation, presence and/or sequence of at least one of said elements has a regulatory effect on the expression of the gene:
(i) a gene coding for a gene product which is expressible in a lactic acid bacterium;
(ii) a promoter element, wherein the function of the promoter element is regulatable by a factor selected from the group consisting of pH, growth temperature, oxygen content, a temperature shift eliciting the expression of heat shock genes, growth medium composition, including the ionic strength and NaCl content, the presence of essential cell constituents or precursors therefor, the growth phase of the bacterium and the growth rate of the bacterium, and
(iii) at least one further nucleotide element, wherein the sequence of said nucleotide element affects the expression of a gene operably linked to the promoter region, wherein the sequence of at least one of said elements is modified relative to the sequence of the corresponding non-modified element,
and further wherein said modification increases the expression level of a gene operably linked to the promoter region by at least two-fold, relative to the expression level, under essentially identical environmental conditions, of the same gene under the control of the corresponding non-modified promoter region,
and further wherein the regulation of the promoter by said factors is not reduced or eliminated by said modification.

25. A lactic acid bacterium according to claim 24 wherein the level at which the gene is expressed is increased at least ten-fold.

26. A lactic acid bacterium according to claim 25 wherein the level at which the gene is expressed is increased at least fifty-fold.

27. A lactic acid bacterium according to claim 26 wherein the level at which the gene is expressed is increased at least one hundred-fold.

28. A method of producing a mycobacterial polypeptide comprising the steps of
(i) isolating a DNA sequence coding for said polypeptide,
(ii) inserting said coding sequence in the vector of claim 1, (iii) transforming a lactic acid bacterium with the vector resulting from step (ii),
(iv) culturing the thus transformed bacterium in a culture medium under conditions where the polypeptide is expressed, and
(v) harvesting the mycobacterial polypeptide.

29. A method according to claim 28 wherein the vector comprises a signal sequence operably linked to the coding sequence.

30. A method according to claim 28 wherein the coding sequence for the mycobacterial polypeptide is derived from *Mycobacterium tuberculosis.*

31. A method according to claim 30 wherein the coding sequence is operably linked to a signal sequence.

32. A method according to claim 30 wherein the polypeptide is an immunologically active polypeptide carrying an epitope or an antigenic determinant, and wherein said polypeptide is capable of stimulating a humoral and/or cellular immune response when administered to an animal.

33. A method according to claim 29 wherein the polypeptide is secreted into the culture medium in an amount of at least 30 mg/l.

34. A method according to claim 28 herein the coding sequence is part of a hybrid coding sequence whereby the polypeptide is expressed as part of a fusion protein.

35. A method according to claim 34 wherein the fusion protein comprises at least two polypeptides of mycobacterial origin.

36. A method according to claim 35 wherein the fusion protein comprises at least two polypeptides of mycobacterial origin having the same amino acid sequence.

37. A method according to claim 34 wherein the fusion protein comprises at least two polypeptides of *Mycobacterium tuberculosis* origin.

38. A method according to claim 37 wherein the fusion protein comprises at least two polypeptides of *Mycobacterium tuberculosis* origin having the same amino acid sequence.

39. A method according to claim 34 wherein the hybrid coding sequence is operably linked to a sequence coding for a signal peptide to provide secretion of the fusion protein across the cell membrane.

40. A method according to claim 28 wherein the lactic acid bacterium is *Lactococcus lactis.*

41. A method of producing a food product comprising adding to the food product starting materials a lactic acid bacterial starter culture according to claim 14.

42. A method of producing an animal feed comprising adding to the feed components a lactic acid bacterial starter culture according to claim 14.

43. A method of producing a pharmaceutically active gene product, the method comprising cultivating a lactic acid bacterial cell according to claim 13, which comprises a gene coding for a pharmaceutically active gene product under conditions where the gene is expressed, and isolating the gene product.

44. A method of producing an immunologically active gene product, the method comprising cultivating a lactic acid bacterial cell according to claim 13, which comprises a gene coding for the immunologically active gene product under conditions where the gene is expressed, and isolating the gene product.

45. A method according to claim 44 wherein the gene product is selected from the group consisting of an epitope, a polypeptide comprising an epitope, an antibody, a monoclonal antibody, an antibody fragment and a derivative of an antibody.

* * * * *